(12) United States Patent
Miller et al.

(10) Patent No.: US 10,889,053 B1
(45) Date of Patent: Jan. 12, 2021

(54) CUSTOM SURGICAL DEVICES AND METHOD FOR MANUFACTURING THE SAME

(71) Applicant: RESTOR3D, INC., Durham, NC (US)

(72) Inventors: Andrew Todd Miller, Raleigh, NC (US); Nathan Timothy Evans, Durham, NC (US)

(73) Assignee: RESTOR3D, INC., Durham, NC (US)

( * ) Notice: Subject to any disclaimer, the term of this patent is extended or adjusted under 35 U.S.C. 154(b) by 0 days.

(21) Appl. No.: 16/557,550

(22) Filed: Aug. 30, 2019

Related U.S. Application Data

(60) Provisional application No. 62/823,224, filed on Mar. 25, 2019.

(51) Int. Cl.
| | |
|---|---|
| *B29C 64/106* | (2017.01) |
| *A61B 17/00* | (2006.01) |
| *A61B 17/16* | (2006.01) |
| *G16H 30/20* | (2018.01) |
| *B33Y 80/00* | (2015.01) |
| *B33Y 10/00* | (2015.01) |
| *B33Y 70/00* | (2020.01) |
| *B33Y 50/02* | (2015.01) |
| *B29L 31/00* | (2006.01) |

(52) U.S. Cl.
CPC ........ *B29C 64/106* (2017.08); *A61B 17/1659* (2013.01); *A61B 2017/00526* (2013.01); *B29L 2031/753* (2013.01); *B33Y 10/00* (2014.12); *B33Y 50/02* (2014.12); *B33Y 70/00* (2014.12); *B33Y 80/00* (2014.12); *G16H 30/20* (2018.01)

(58) Field of Classification Search
CPC ..... B29C 64/106; B29C 64/124; B33Y 50/02; B33Y 10/00; B33Y 80/00; B33Y 70/00; A61B 2017/00526; A61B 17/1659
See application file for complete search history.

(56) References Cited

U.S. PATENT DOCUMENTS

| | | | |
|---|---|---|---|
| 4,440,835 A | | 4/1984 | Vignaud |
| 4,588,574 A | * | 5/1986 | Felder ............... A61K 49/0404 424/9.41 |
| 5,248,456 A | * | 9/1993 | Evans, Jr. ................ B08B 3/12 264/401 |
| 7,001,672 B2 | | 2/2006 | Justin et al. |
| 7,632,575 B2 | | 12/2009 | Justin et al. |

(Continued)

OTHER PUBLICATIONS

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).*

(Continued)

*Primary Examiner* — Galen H Hauth
(74) *Attorney, Agent, or Firm* — Morris, Manning & Martin, LLP; Bryan D. Stewart

(57) ABSTRACT

The present disclosure relates generally to custom medical devices and additive manufacturing (3D printing) processes for producing the same. Using certain materials and novel fabrication techniques, the present systems and methods can directly print nearly any size or shape medical device or instrument. For example, in certain embodiments, the present systems and methods leverage stereolithography ("SLA") and photo-curable polymers to produce custom, radiopaque medical devices and instruments.

25 Claims, 18 Drawing Sheets

(56) References Cited

U.S. PATENT DOCUMENTS

| | | |
|---|---|---|
| 7,666,522 B2 | 2/2010 | Justin et al. |
| 8,142,886 B2 | 3/2012 | Noble et al. |
| 8,430,930 B2 | 4/2013 | Hunt |
| 8,457,930 B2 | 6/2013 | Schroeder |
| 8,485,820 B1 | 7/2013 | Ali |
| 8,551,173 B2 | 10/2013 | Lechmann et al. |
| 8,775,133 B2 | 7/2014 | Schroeder |
| 8,828,311 B2 | 9/2014 | Medina et al. |
| 8,843,229 B2 | 9/2014 | Vanasse et al. |
| 8,888,485 B2 | 11/2014 | Ali |
| 9,034,237 B2 * | 5/2015 | Sperry ............... B29C 67/0077 264/401 |
| 9,180,029 B2 | 11/2015 | Hollister et al. |
| 9,186,257 B2 | 11/2015 | Geisler et al. |
| 9,271,845 B2 | 3/2016 | Hunt et al. |
| 9,295,562 B2 | 3/2016 | Lechmann et al. |
| 9,308,060 B2 | 4/2016 | Ali |
| 9,339,279 B2 | 5/2016 | Dubois et al. |
| 9,364,896 B2 | 6/2016 | Christensen et al. |
| 9,370,426 B2 | 6/2016 | Gabbrielli et al. |
| 9,421,108 B2 | 8/2016 | Hunt |
| 9,433,510 B2 | 9/2016 | Lechmann et al. |
| 9,433,707 B2 | 9/2016 | Swords et al. |
| 9,545,317 B2 | 1/2017 | Hunt |
| 9,549,823 B2 | 1/2017 | Hunt et al. |
| 9,561,115 B2 | 2/2017 | Elahinia et al. |
| 9,572,669 B2 | 2/2017 | Hunt et al. |
| 9,597,197 B2 | 3/2017 | Lechmann et al. |
| 9,636,226 B2 | 5/2017 | Hunt |
| 9,649,178 B2 | 5/2017 | Ali |
| 9,662,157 B2 | 5/2017 | Schneider et al. |
| 9,662,226 B2 | 5/2017 | Wickham |
| 9,668,863 B2 | 6/2017 | Sharp et al. |
| 9,675,465 B2 | 6/2017 | Padovani et al. |
| 9,688,026 B2 | 6/2017 | Ho et al. |
| 9,694,541 B2 | 7/2017 | Pruett et al. |
| 9,715,563 B1 | 7/2017 | Schroeder |
| 9,757,235 B2 | 9/2017 | Hunt et al. |
| 9,757,245 B2 | 9/2017 | O'Neil et al. |
| 9,782,270 B2 | 10/2017 | Wickham |
| 9,788,972 B2 | 10/2017 | Flickinger et al. |
| 9,907,670 B2 | 3/2018 | Deridder et al. |
| 9,910,935 B2 | 3/2018 | Golway et al. |
| 9,918,849 B2 | 3/2018 | Morris et al. |
| 9,943,627 B2 | 4/2018 | Zhou et al. |
| 10,183,442 B1 | 1/2019 | Miller |
| 10,245,152 B2 | 4/2019 | Kloss |
| 10,624,746 B2 | 4/2020 | Jones et al. |
| 2004/0148032 A1 | 7/2004 | Rutter et al. |
| 2007/0118243 A1 | 5/2007 | Schroeder et al. |
| 2008/0206297 A1 | 8/2008 | Roeder et al. |
| 2009/0093668 A1 | 4/2009 | Marten et al. |
| 2010/0137990 A1 | 6/2010 | Apatsidis et al. |
| 2010/0286791 A1 | 11/2010 | Goldsmith |
| 2011/0144752 A1 | 6/2011 | Defelice et al. |
| 2011/0224796 A1 | 9/2011 | Weiland et al. |
| 2011/0230974 A1 | 9/2011 | Musani |
| 2012/0064288 A1 | 3/2012 | Nakano et al. |
| 2012/0215310 A1 | 8/2012 | Sharp et al. |
| 2013/0123935 A1 | 5/2013 | Hunt et al. |
| 2013/0158651 A1 | 6/2013 | Hollister et al. |
| 2013/0197657 A1 | 8/2013 | Anca et al. |
| 2013/0218282 A1 | 8/2013 | Hunt |
| 2014/0107786 A1 | 4/2014 | Geisler et al. |
| 2014/0236299 A1 | 8/2014 | Roeder et al. |
| 2014/0277443 A1 | 9/2014 | Fleury et al. |
| 2014/0288650 A1 | 9/2014 | Hunt |
| 2014/0336680 A1 | 11/2014 | Medina et al. |
| 2014/0371863 A1 | 12/2014 | Vanasse et al. |
| 2015/0105858 A1 | 4/2015 | Papay et al. |
| 2015/0282945 A1 | 10/2015 | Hunt |
| 2015/0282946 A1 | 10/2015 | Hunt |
| 2015/0320461 A1 * | 11/2015 | Ehmke ............... A61B 17/8685 606/67 |
| 2015/0335434 A1 | 11/2015 | Patterson et al. |
| 2015/0343709 A1 | 12/2015 | Gerstle et al. |
| 2015/0351915 A1 | 12/2015 | Defelice et al. |
| 2016/0051371 A1 | 2/2016 | Defelice et al. |
| 2016/0089138 A1 | 3/2016 | Early et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213485 A1 | 7/2016 | Schaufler et al. |
| 2016/0213486 A1 | 7/2016 | Nunley et al. |
| 2016/0213487 A1 | 7/2016 | Wilson et al. |
| 2016/0213488 A1 | 7/2016 | Moore et al. |
| 2016/0220288 A1 | 8/2016 | Dubois et al. |
| 2016/0256279 A1 | 9/2016 | Sanders et al. |
| 2016/0256610 A1 | 9/2016 | Zhou et al. |
| 2016/0270931 A1 | 9/2016 | Trieu |
| 2016/0287388 A1 | 10/2016 | Hunt et al. |
| 2016/0303793 A1 * | 10/2016 | Ermoshkin ............ B33Y 10/00 |
| 2016/0333152 A1 | 11/2016 | Cook et al. |
| 2016/0374829 A1 | 12/2016 | Vogt et al. |
| 2017/0014169 A1 | 1/2017 | Dean et al. |
| 2017/0020685 A1 | 1/2017 | Geisler et al. |
| 2017/0036403 A1 | 2/2017 | Ruff et al. |
| 2017/0042697 A1 | 2/2017 | McShane, III et al. |
| 2017/0056178 A1 | 3/2017 | Sharp et al. |
| 2017/0056179 A1 | 3/2017 | Lorio |
| 2017/0066873 A1 | 3/2017 | Gardet |
| 2017/0105844 A1 | 4/2017 | Kuyler et al. |
| 2017/0156880 A1 | 6/2017 | Halverson et al. |
| 2017/0165085 A1 | 6/2017 | Lechmann et al. |
| 2017/0165790 A1 | 6/2017 | McCarthy et al. |
| 2017/0172758 A1 | 6/2017 | Field et al. |
| 2017/0182222 A1 | 6/2017 | Paddock et al. |
| 2017/0209274 A1 | 7/2017 | Beerens et al. |
| 2017/0216035 A1 | 8/2017 | Hunt |
| 2017/0216036 A1 | 8/2017 | Cordaro |
| 2017/0239054 A1 | 8/2017 | Engstrand et al. |
| 2017/0239064 A1 | 8/2017 | Cordaro |
| 2017/0245998 A1 | 8/2017 | Padovani et al. |
| 2017/0252165 A1 | 9/2017 | Sharp et al. |
| 2017/0258606 A1 | 9/2017 | Afzal |
| 2017/0282455 A1 | 10/2017 | Defelice et al. |
| 2017/0296244 A1 | 10/2017 | Schneider et al. |
| 2017/0319344 A1 | 11/2017 | Hunt |
| 2017/0323037 A1 | 11/2017 | Schroeder |
| 2017/0333205 A1 | 11/2017 | Joly et al. |
| 2017/0354510 A1 | 12/2017 | O'Neil et al. |
| 2017/0354513 A1 | 12/2017 | Maglaras et al. |
| 2017/0355815 A1 | 12/2017 | Becker et al. |
| 2017/0360488 A1 | 12/2017 | Kowalczyk et al. |
| 2017/0360563 A1 | 12/2017 | Hunt et al. |
| 2017/0360578 A1 | 12/2017 | Shin et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0022017 A1 | 1/2018 | Fukumoto et al. |
| 2018/0064540 A1 | 3/2018 | Hunt |
| 2018/0085230 A1 | 3/2018 | Hunt |
| 2018/0104063 A1 | 4/2018 | Asaad |
| 2018/0110593 A1 | 4/2018 | Khalil |
| 2018/0110626 A1 | 4/2018 | McShane, III et al. |
| 2018/0110627 A1 | 4/2018 | Sack |
| 2018/0117219 A1 * | 5/2018 | Yang ..................... A61L 31/06 |
| 2018/0147319 A1 | 5/2018 | Colucci-Mizenko et al. |
| 2018/0289515 A1 | 10/2018 | Nemes et al. |
| 2019/0262101 A1 | 8/2019 | Shanjani et al. |
| 2019/0343652 A1 | 11/2019 | Petersheim et al. |
| 2020/0030102 A1 | 1/2020 | Mullens et al. |
| 2020/0046512 A1 | 2/2020 | Newman et al. |

OTHER PUBLICATIONS

Rozema et al., The effects of different steam-sterilization programs on material properties of poly(l-lactide), Journal of Applied Biomaterials, vol. 2, 23-28 (1991) (Year: 1991).*

Alt, Sami, "Design for Sterilization Part 1: Steam Sterillization." Material, Material Technology Blog, Jun. 3, 2016, www.material-technology.com/single-post/2016/05/24/Design-for-Sterilization-part-1-Steam-Sterillization.

(56) References Cited

OTHER PUBLICATIONS

Ducheyne, Paul, "Comprehensive Biomaterials." Comprehensive Biomaterials, vol. 1, Elsevier, 2011, pp. 135-135.
Andrew T. Miller et al., Deformation and Fatigue of Tough 30 Printed Elastomer Scaffolds Processed by Fused 3 Deposition Modeling and Continuous Liquid Interface Production, 75 J. Mechanical Behavior Biomedical Materials 1 (2017).
Andrew T. Miller et al., Fatigue of Injection Molded and 30 Printed Polycarbonate Urethane in Solution, 108 Polymer 121 (2017).
Anat Ratnovsky et al., Mechanical Properties of Different Airway Stents, Med. Eng'G. Physics, Mar. 2011, at 408., http://www.medengphys.com/article/S1350-4533(15)00042-9/fulltext.

\* cited by examiner

FIG. 8

| ID | Date Opened | Last Modified | Patient | Device | Status | Images | Models |
|---|---|---|---|---|---|---|---|
| AdamsS_C1P18 | | 19 days ago | | No Device Needed | Downloaded by restor3d | 394 | 0 |
| AdamsS_C1P17 | | 19 days ago | | No Device Needed | Downloaded by restor3d | 317 | 0 |
| AdamsS_C1P16 | | 2 months ago | | Unknown Device | Downloaded by restor3d | 468 | 0 |
| AdamsS_C1P15 | | 2 months ago | | Ankle Cage | Design Proposal Uploaded | 1029 | 1 |
| AdamsS_C1P14 | | 2 months ago | | Unknown Device | Design Proposal Uploaded | 1261 | 1 |
| AdamsS_C1P13 | | 2 months ago | | Unknown Device | Devices Delivered | 309 | 1 |
| AdamsS_C1P12 | | 3 months ago | | Unknown Device | Downloaded by restor3d | 234 | 0 |
| AdamsS_C1P10 | | 3 months ago | | No Device Needed | Downloaded by restor3d | 533 | 0 |
| AdamsS_C1P10 | | 3 months ago | | Distal Tibia Replacement Device | Devices Delivered | 362 | 1 |
| AdamsS_C1P9 | | 5 months ago | | Distal Tibia Replacement Device | Design Proposal Uploaded | 249 | 1 |

FIG. 10

CUSTOM SURGICAL DEVICES AND METHOD FOR MANUFACTURING THE SAME

CROSS REFERENCE TO RELATED APPLICATIONS

This application claims the benefit of and priority to U.S. Patent Application No. 62/823,224 filed Mar. 25, 2019, entitled "METHOD FOR MANUFACTURING RADIOPAQUE PHOTO-CURED POLYMER DEVICES," which is incorporated herein by reference in its entirety.

TECHNICAL FIELD

The present systems, methods, and apparatuses relate generally to manufacturing surgical devices.

BACKGROUND

Devices (e.g., inserters, trials, tamps, rasps, etc.) utilized by a surgeon during various surgeries are traditionally made from metal, namely stainless steel, and are intended to be reprocessed (e.g., cleaned and sterilized) and reused. Accordingly, these previous devices are typically made from a standard design that may not substantially conform to one or more dimensions of a particular patient. Furthermore, in instances where a device is ill-suited to performing a specific surgical task within a specific patient, a surgeon is left with little recourse, as they must a) attempt to proceed with utilizing the ill-suited device or b) wait for device industry entities to produce a more suitable device (which may never occur, depending on a variety of, predominantly economic, factors). Using previous devices and manufacturing techniques, customized device fabrication may be prohibitively costly and/or logistically infeasible (for example, due to production workload constraints), thus there exists a need for devices and fabrication techniques that can facilitate customization without presenting prohibitive costs and logistical barriers.

Even in instances where a patient can afford a custom device, required lead times for traditional custom fabrication methods may be prohibitively high and many patients requiring surgery cannot afford to wait for such extended fabrication times. Some previous solutions to surgical device fabrication do not provide for custom device fabrication services in any capacity (e.g., due to associated expenses and inability to generate profit at low production volumes). Thus, there exists a growing need for: 1) disposable surgical devices that incorporate custom designs and that can be promptly produced in an economically efficient manner; and 2) an interface that streamlines and facilitates a custom device and fabrication process.

BRIEF SUMMARY

Provided herein are descriptions of custom, disposable devices and methods for producing the same.

In various embodiments, the present devices may be formed from a photo-curable polymer, wherein the polymer may be doped with an imaging contrast agent. In at least one embodiment, the imaging contrast agent results in devices (produced from the doped polymer) that are radiopaque. In one or more embodiments, the present devices may be formed using additive manufacturing methods (for example, stereolithography). Because the present devices are disposable and sourced from custom designs (which may be frequently iterated upon), production via additive manufacturing may reduce manufacturing complexity and cost. For example, whereas manufacture of non-disposable instruments (which typically consist of stainless steel) requires expensive casting and machining equipment, manufacture of disposable instruments via additive manufacturing may require no molds and minimal machining. In one or more embodiments, the capability of the present devices to be produced via additive manufacturing provides production advantages including, but not limited to: 1) increased capacity for complexity (because additive manufacturing may be capable of forming geometries that are infeasible by traditional manufacturing methods); 2) increased capacity for variety (e.g., because an additive manufacturing line can be configured to produce multiple product types); 3) reduction of required manufacturing lead time; 4) reduction of material waste and, thus, material expenses; and 5) increased spectrum of manufacturing materials.

In at least one embodiment, the present devices may be disposable. Device disposability may reduce manufacturing cost, simplify inventory management, and allow for more opportunity to iterate on designs. In various embodiments, a disposable device must satisfy clinical and user criteria that may be associated with surgical instrumentation. In one embodiment, clinical and user criteria may include, but are not limited to, device strength, stiffness, toughness, biocompatibility and visibility with imaging modalities (e.g., X-ray, etc.). Accordingly, in at least one embodiment, the present devices may demonstrate physical properties that are sufficient to satisfy the clinical and user criteria.

In various embodiments, present methods include preparation of a resin that may be doped with an imaging contrast agent, which may be of a particular particle size. In one or more embodiments, devices may be manufactured from doped resin using additive manufacturing techniques (e.g., stereolithography), wherein the resulting devices are radiopaque (e.g., visible with imaging modalities) and also satisfy clinical and user criteria. In at least one embodiment, the imaging contrast agent may be barium sulfate. In one or more embodiments, doping and mixing of the resin may be optimized, according to one or more present methods, to result in a polymer-based radiopaque device with adequate imaging contrast, but not result in significant degradation of device mechanical properties and/or other device attributes including, but not limited to, manufacturability, surface finish, and overall aesthetics.

Prior to experimentation performed herein, doping of a photo-curable polymer with barium sulfate was not expected to produce a doped resin suitable for fabricating radiopaque devices. Mixing, forming and curing a photo-curable polymer is a delicate process, and effects of adding a foreign agent to the polymer prior to curing were unknown. Due to an observed tendency of barium sulfate to form clumps, it was expected that the addition of barium sulfate to a photo-curable polymer may render the polymer unusable in further additive manufacturing processes (e.g., due to prohibitively high viscosity, clogs, etc.). Furthermore, one would expect that doping of a photo-curable polymer with a foreign agent, like barium sulfate would decrease desired mechanical properties upon curing.

However, as described herein, doping of a photo-curable polymer with barium sulfate yielded a doped resin that, unexpectedly, remained suitable for use in an additive manufacturing process, and that was successfully formed (using the additive process) into a radiopaque device with comparable (if not improved) mechanical properties. In summary, successful results observed in producing a doped resin and (from the doped resin) a radiopaque device were unexpected.

In various embodiments, present methods include a custom manufacturing process. In one or more embodiments, the custom manufacturing process may include, but is not limited to: 1) one or more methods of processing an imaging contrast agent; 2) one or more methods of doping and mixing uncured resin with a processed imaging contrast agent; and 3) one or more methods of modifying existing 3D printing infrastructure (e.g., resin cartridges) to improve printing outcomes, wherein the printing utilizes doped resin and outcomes include custom polymer-based radiopaque devices (e.g., instruments) with sufficient device strength, stiffness, toughness, and biocompatibility for use in a surgical setting.

In at least one embodiment, the present disclosure provides an electronic application for facilitating and monitoring a custom device design and fabrication process. In various embodiments, the application may include at least one server, at least one processor and memory. In one or more embodiments, the application may include a surgeon portion that allows a surgeon to upload a device design request and associated data (e.g., patient medical images, etc.), and commission design and fabrication of a custom device. In one embodiment, the application may include a designer portion that allows a designer to view a custom device design and fabrication request (and associated and, in some embodiments, anonymized data), communicate with a surgeon regarding the design request and upload custom device designs (e.g., for review by a surgeon). In at least one embodiment, the electronic application may provide a means for tracking and managing aspects of a custom device design and fabrication process including, but not limited to: 1) custom device design and revision; 2) custom device fabrication; 3) custom device shipment; and 4) custom device design collaboration (e.g., amongst two or more surgeons).

According to a first aspect, a method for producing disposable, radiopaque devices including: A) normalizing a quantity of barium sulfate particles, wherein normalizing includes milling and sieving the quantity of barium sulfate particles; B) mixing a substantially homogenous photo-curable mixture including approximately 1-10% weight percent of the normalized barium sulfate particles and approximately 90-99% weight percent of a resin, wherein the photo-curable mixture has a higher viscosity than the resin; C) 3D printing the photo-curable mixture in a particular shape by: 1) mixing the photo-curable mixture via a wiper arm; and 2) printing the photo-curable mixture in the particular shape; D) curing the 3D-printed photo-curable mixture in the particular shape by heating the 3D-printed photo-curable mixture and bathing the 3D-printed photo-curable mixture in light to create a radiopaque device including a first ultimate bending strength and a first bending yield strength; and E) autoclaving the radiopaque device, wherein: 1) the autoclaved, radiopaque device includes a second ultimate bending strength and a second bending yield strength; 2) the second ultimate bending strength is greater than the first ultimate bending strength; and 3) the second bending yield strength is greater than the first bending yield strength.

According to a second aspect, the method of for producing disposable, radiopaque devices of the first aspect or any other aspect, wherein: A) the second ultimate bending strength is about 4-10% greater than the first ultimate bending strength; and B) the second bending yield strength is about 5-9% greater than the first bending yield strength.

According to a third aspect, the method for producing disposable, radiopaque devices of the first aspect or any other aspect, wherein the autoclaved, radiopaque device includes: A) an ultimate tensile strength between about 26-32 MPa; and B) a tensile yield strength between about 16-25 MPa.

According to a fourth aspect, the method for producing disposable, radiopaque devices of the third aspect or any other aspect, wherein curing the 3D-printed photo-curable mixture includes: A) heating the radiopaque 3D-printed photo-curable mixture to about 60 degrees Celsius; and B) bathing the radiopaque 3D-printed photo-curable mixture in about 405 nm light.

According to a fifth aspect, the method for producing disposable, radiopaque devices of the fourth aspect or any other aspect, wherein autoclaving the radiopaque device includes steam autoclaving the radiopaque device at a temperature of about 132 degrees Celsius.

According to a sixth aspect, the method for producing disposable, radiopaque devices of the firth aspect or any other aspect, wherein the substantially homogenous photo-curable mixture is mixed in a mixer with sharp blades.

According to a seventh aspect, the method for producing disposable, radiopaque devices of the sixth aspect or any other aspect, wherein the photo-curable mixture is printed via a stereolithography 3D-printer.

According to an eighth aspect, the method for producing disposable, radiopaque devices of the seventh aspect or any other aspect, wherein the autoclaved, radiopaque device is viewable via at least one radiative imaging technique.

According to a ninth aspect, the method for producing disposable, radiopaque devices of the eighth aspect or any other aspect, wherein the radiopaque device includes a drain port.

According to a tenth aspect, the method for producing disposable, radiopaque devices of the ninth aspect or any other aspect, wherein the drain port is integrally formed within the radiopaque device.

According to an eleventh aspect, the method for producing disposable, radiopaque devices of the tenth aspect or any other aspect, wherein the drain port includes: A) a generally cylindrical cross-section; and B) at least one bend.

According to a twelfth aspect, the method for producing disposable, radiopaque devices of the eleventh aspect or any other aspect, wherein the drain port includes one or more threads.

According to a thirteenth aspect, the method for producing disposable, radiopaque devices of the ninth aspect or any other aspect, further including draining uncured photo-curable mixture from the radiopaque device via the drain port.

According to a fourteenth aspect, a method for producing disposable, radiopaque devices including: A) mixing a substantially homogenous photo-curable mixture including approximately 1-10% weight percent of the radiographic contrast agent particles and approximately 90-99% weight percent of a resin, wherein the photo-curable mixture has a higher viscosity than the resin; B) 3D printing the photo-curable mixture in a particular shape; C) curing the 3D-printed photo-curable mixture in the particular shape by heating the 3D-printed photo-curable mixture and bathing the 3D-printed photo-curable mixture in light to create a radiopaque device including a first ultimate bending strength and a first bending yield strength; and D) autoclaving the radiopaque device, wherein: 1) the autoclaved, radiopaque device includes a second ultimate bending strength and a second bending yield strength; 2) the second ultimate bending strength is greater than the first ultimate bending strength; and 3) the second bending yield strength is greater than the first bending yield strength.

According to a fifteenth aspect, a method for producing disposable, radiopaque devices of the fourteenth aspect or any other aspect, wherein the radiopaque device includes: A) an ultimate tensile strength between about 26-32 MPa; and B) a tensile yield strength between about 16-25 MPa.

According to a sixteenth aspect, the method for producing disposable, radiopaque devices of the fourteenth aspect or any other aspect, wherein curing the 3D-printed photo-curable mixture includes: A) heating the radiopaque 3D-printed photo-curable mixture to about 60 degrees Celsius; and B) bathing the radiopaque 3D-printed photo-curable mixture in about 405 nm light.

According to a seventeenth aspect, the method for producing disposable, radiopaque devices of the sixteenth aspect or any other aspect, wherein autoclaving the radiopaque device includes steam autoclaving the radiopaque device at a temperature of about 132 degrees Celsius.

According to an eighteenth aspect, the method for producing disposable, radiopaque devices of the seventeenth aspect or any other aspect, wherein the substantially homogenous photo-curable mixture is mixed in a mixer with sharp blades.

According to a nineteenth aspect, the method for producing disposable, radiopaque devices of the eighteenth aspect or any other aspect, wherein the photo-curable mixture is printed via a stereolithography 3D-printer.

According to a twentieth aspect, the method for producing disposable, radiopaque devices of the nineteenth aspect or any other aspect, wherein the autoclaved, radiopaque device is viewable via at least one radiative imaging technique.

According to a twenty-first aspect, the method for producing disposable, radiopaque devices of the twentieth aspect or any other aspect, wherein the radiopaque device includes a drain port.

According to a twenty-second aspect, the method for producing disposable, radiopaque devices of the twenty-first aspect or any other aspect, wherein the drain port is integrally formed within the radiopaque device.

According to a twenty-third aspect, the method for producing disposable, radiopaque devices of the twenty-second aspect or any other aspect, wherein the drain port includes: A) a generally cylindrical cross-section; and B) at least one bend.

According to a twenty-fourth aspect, the method for producing disposable, radiopaque devices of the twenty-third aspect or any other aspect, wherein the drain port includes one or more threads.

According to a twenty-fifth aspect, the method for producing disposable, radiopaque devices of the twenty-third aspect or any other aspect, further including draining uncured photo-curable mixture from the radiopaque device via the drain port.

According to a twenty-sixth aspect, the method for producing disposable, radiopaque devices of the fourteenth aspect or any other aspect, further including normalizing a quantity of radiographic contrast agent particles, wherein normalizing includes milling and sieving the quantity of radiographic contrast agent particles.

According to a twenty-seventh aspect, the method for producing disposable, radiopaque devices of the fourteenth aspect or any other aspect, wherein the radiographic contrast agent particles include barium sulfate particles.

According to a twenty-eighth aspect, a surgical device including: A) a 3D-printed body including photo-cured resin including between about 90-99% by weight resin and barium sulfate between about 1-10% by weight, wherein: 1) the 3D-printed body is radiopaque and viewable via at least one radiative imaging technique; and 2) the 3D-printed body is autoclaved; B) an ultimate tensile strength between about 26-32 MPa; and C) a tensile yield strength between about 16-25 MPa.

According to a twenty-ninth aspect, the surgical device of the twenty-eighth aspect or any other aspect, wherein prior to autoclaving, the 3D-printed body includes: A) a post-autoclave ultimate bending strength; B) a post-autoclave bending yield strength; C) a pre-autoclave ultimate bending strength that is about 4-10% less than the post-autoclave ultimate bending strength; and D) a pre-autoclave bending yield strength that is about 5-9% less than the post-autoclave bending yield strength.

According to a thirtieth aspect, the surgical device of the twenty-eighth aspect or any other aspect, wherein the 3D-printed body is cured by: A) heating the 3D-printed body to about 60 degrees Celsius; and B) bathing the 3D-printed body in about 405 nm light.

According to a thirty-first aspect, the surgical device of the twenty-eighth aspect or any other aspect, wherein the resin and barium sulfate are generally homogenously mixed prior to 3D-printing the body or photo-curing.

According to a thirty-second aspect, the surgical device of the twenty-eighth aspect or any other aspect, wherein the resin and barium sulfate mixture has a higher viscosity than the resin.

According to a thirty-third aspect, the surgical device of the twenty-eighth aspect or any other aspect, including a drain port integrally formed within the 3D-printed body for draining uncured resin.

According to a thirty-fourth aspect, the surgical device of the thirty-third aspect or any other aspect, wherein the drain port has a generally cylindrical cross-section.

According to a thirty-fifth aspect, the surgical device of the thirty-third aspect or any other aspect, wherein the drain port includes one or more threads.

According to a thirty-sixth aspect, the surgical device of the thirty-thirty aspect or any other aspect, wherein the drain port includes at least one bend.

According to a thirty-seventh aspect, the surgical device of the twenty-eighth aspect or any other aspect, wherein the radiopaque 3D-printed body is a disposable surgical instrument for inserting an implant into a patient.

According to a thirty-eighth aspect, a disposable surgical instrument for implanting a device within a patient including: A) an autoclaved, radiopaque 3D-printed body including: B) a photo-cured resin including between about 90-99% by weight resin and barium sulfate between about 1-10% by weight, wherein the photo-cured resin renders the 3D-printed body radiopaque; C) an ultimate tensile strength between about 26-32 MPa; D) a tensile yield strength between about 16-25 MPa; E) a drain port integrally formed within the radiopaque 3D-printed body including a generally cylindrical cross-section, one or more threads, and at least one bend for draining uncured resin, wherein: 1) the photo-cured resin is cured by: I) heating the radiopaque 3D-printed body to about 60 degrees Celsius; and II) bathing the radiopaque 3D-printed body in about 405 nm light; 2) the resin and barium sulfate are generally homogenously mixed prior to 3D-printing the body or photo-curing; and 3) the radiopaque 3D-printed body is viewable via at least one radiative imaging technique.

According to a thirty-ninth aspect, the surgical device of the thirty-eighth aspect or any other aspect, wherein the homogenous resin and barium sulfate mixture has a higher viscosity than the resin.

According to a fortieth aspect, the surgical device of the thirty-eighth aspect or any other aspect, wherein the radiopaque 3D-printed body includes one or more text features.

According to a forty-first aspect, a disposable surgical instrument for implanting a device within a patient including: A) a 3D-printed body including: 1) a photo-cured resin including between about 90-99% by weight resin and barium sulfate between about 1-10% by weight, wherein the photo-cured resin renders the 3D-printed body radiopaque; 2) a first ultimate bending strength; and 3) a first yield strength; and B) a drain port integrally formed within the 3D-printed body including a generally cylindrical cross-section, one or more threads, and at least one bend for draining uncured resin, wherein after autoclaving, the 3D-printed body is viewable via at least one radiative imaging technique and the autoclaved, 3D-printed body includes: A) a second ultimate bending strength; and B) a second bending yield strength, wherein: I) the second ultimate bending strength is greater than the first ultimate bending strength; and II) the second bending yield strength is greater than the first bending yield strength.

According to a forty-second aspect, the disposable surgical instrument of the forty-first aspect or any other aspect, wherein the radiopaque 3D-printed body is viewable via at least one radiative imaging technique prior to autoclaving.

According to a forty-third aspect, the disposable surgical instrument of the forty-second aspect or any other aspect, wherein the photo-cured resin is cured by: A) heating the 3D-printed body to about 60 degrees Celsius; and B) bathing the 3D-printed body in about 405 nm light.

According to a forty-fourth aspect, the disposable surgical instrument of the forty-third aspect or any other aspect, wherein the resin and barium sulfate are generally homogenously mixed prior to 3D-printing the body and photo-curing.

According to a forty-fifth aspect, the disposable surgical instrument of the forty-fourth aspect or any other aspect, wherein the resin and barium sulfate mixture are 3D-printed via a stereolithography 3D-printer.

According to a forty-sixth aspect, the disposable surgical instrument of the forty-fifth aspect or any other aspect, wherein the 3-D printed body further includes: A) an ultimate tensile strength between about 26-32 MPa; and B) a tensile yield strength between about 16-25 MPa.

According to a forty-seventh aspect, a method for producing disposable, radiopaque devices including: A) normalizing a quantity of radiographic contrast agent particles; B) creating a photo-curable mixture including approximately 1-10% weight percent of the normalized radiographic contrast agent particles and approximately 90-99% weight percent of a resin; C) 3D printing the photo-curable mixture in a particular shape; and D) curing the 3D-printed photo-curable mixture in the particular shape, wherein the cured, 3D-printed photo-curable mixture in the particular shape is radiopaque.

According to a forty-eighth aspect, the method of the forty-seventh aspect or any other aspect, wherein creating the photo-curable mixture includes mixing the normalized radiographic contrast agent particles and the resin with an electric mixer with sharp blades.

According to a forty-ninth aspect, the method of the twenty-first aspect or any other aspect, wherein the photo-curable mixture is generally homogenous.

According to a fiftieth aspect, the method of the forty-ninth aspect or any other aspect, wherein the photo-curable mixture has a higher viscosity than the resin.

According to a fifty-first aspect, the method of the fiftieth aspect or any other aspect, wherein the method further includes: A) filling one or more cartridges with the photo-curable mixture prior to 3D printing the photo-curable mixture; and B) modifying an outlet of each of the one or more cartridges to accommodate for photo-curable mixture's higher viscosity.

According to a fifty-second aspect, the method of the fiftieth aspect or any other aspect, wherein 3D printing the photo-curable mixture in the particular shape includes mixing the photo-curable mixture via a wiper arm.

According to a fifty-third aspect, the method of the fiftieth aspect or any other aspect, wherein curing the 3D-printed photo-curable mixture in the particular shape includes: A) heating the 3D-printed photo-curable mixture to about 60 degrees Celsius; and B) bathing the 3D-printed photo-curable mixture in about 405 nm light.

According to a fifty-fourth aspect, the method of the fiftieth aspect or any other aspect, wherein the radiographic contrast agent is barium sulfate.

According to a fifty-fifth aspect, a method for producing disposable, radiopaque devices including: A) normalizing a quantity of barium sulfate particles, wherein normalizing includes milling and sieving the quantity of barium sulfate particles; B) mixing, in a mixer with sharp blades, a homogenous photo-curable mixture including approximately 1-10% weight percent of the normalized barium sulfate particles and approximately 90-99% weight percent of a resin, wherein the photo-curable mixture has a higher viscosity than the resin; C) 3D printing the photo-curable mixture in a particular shape with at least one drain port for draining uncured resin, the 3D printing including: 1) filling, with the photo-curable mixture, a resin reservoir in excess of an indicated filling volume; 2) mixing the photo-curable mixture via a wiper arm; and 3) printing the photo-curable mixture in the particular shape; D) curing the 3D-printed photo-curable mixture in the particular shape, wherein: 1) the cured, 3D-printed photo-curable mixture in the particular shape is radiopaque; and 2) curing further includes: I) heating the 3D-printed photo-curable mixture; and II) bathing the 3D-printed photo-curable mixture in light; and E) draining uncured resin, via the drain port, from the particular shape.

According to a fifty-sixth aspect, the method of the fifty-fifth aspect or any other aspect, wherein 3D-printing the photo-curable mixture in the particular shape further includes receiving a CAD file including the particular shape.

According to a fifty-seventh aspect, the method of the fifty-sixth aspect or any other aspect, wherein the particular shape is a medical device instrument shape for a standard-sized medical device.

According to a fifty-eighth aspect, the method of the fifty-sixth aspect or any other aspect, wherein the particular shape is a custom medical device instrument shape.

According to a fifty-ninth aspect, the method of the fifty-eighth aspect or any other aspect, wherein the custom medical device instrument shape is received from a software system for designing custom medical device instrument shapes.

According to a sixtieth aspect, a method for imaging a surgical device, including: A) inserting at least a portion of a surgical device into a patient, the surgical device including: 1) photo-cured resin between about 90-99% by weight; 2) normalized barium sulfate including between about 1-10%, wherein the barium sulfate renders the surgical device radiopaque; 3) an ultimate tensile strength between about 26-32 MPa; and 4) a tensile yield strength between about 16-25 MPa; and B) imaging the surgical device with at least one radiative imaging source.

According to a sixty-first aspect, a method for inserting an implant including: A) removably attaching an implant to a surgical device, the surgical device including: 1) an ultimate tensile strength between about 26-32 MPa; 2) a tensile yield strength between about 16-25 MPa; 3) photo-cured resin including: I) between about 90-99% by weight; and II) normalized barium sulfate including between about 1-10% by weight, wherein the barium sulfate renders the surgical device radiopaque; and 3) an integrally formed spout for draining uncured resin out of the surgical device; B) imaging the surgical device with at least one radiative imagine source; C) while imaging the surgical device, orienting the surgical device to a target site; and D) removing the implant from the surgical device into the target site.

According to a sixty-second aspect, a radiopaque material including: A) between about 90-99% by weight resin; and B) normalized barium sulfate including between about 1-10% by weight, wherein: 1) the barium sulfate renders the radiopaque material viewable via at least one radiative imaging source; and 2) the radiopaque material has a higher viscosity than the resin.

According to a sixty-third aspect, the radiopaque material of the sixty-second aspect or any other aspect, wherein: A) after SLA 3D-printing the radiopaque material into a sample with a minimum cross-sectional area and subjecting the sample to a curing process by a) heating the sample to about 60 degrees Celsius; and b) bathing the sample in about 405 nm light, wherein the sample includes: 1) an ultimate bending strength between about 225-240 N when tested under a three-point bending test with a support span of about 128 mm; and 2) a bending yield strength between about 220-230 N when tested under the three-point bending test with the support span.

According to a sixty-fourth aspect, the radiopaque material of the sixty-third aspect or any other aspect, wherein, after subjecting the sample to the curing process and a steam autoclaving process at a temperature of about 132 degrees Celsius for about 4 minutes, the sample includes: A) an ultimate bending strength between about 240-265 N when tested under the three-point bending test with the support span; and B) a bending yield strength between about 230-260 N when tested under the three-point bending test with the support span.

According to a sixty-fifth aspect, the radiopaque material of the sixty-fourth aspect or any other aspect, wherein, after subjecting the sample to the curing and steam autoclaving processes, the sample includes: A) an ultimate tensile strength between about 26-32 MPa; and B) a tensile yield strength between about 16-25 MPa.

According to a sixty-sixth aspect, the radiopaque material of the sixty-fifth aspect or any other aspect, wherein, after subjecting the sample to the curing and steam autoclaving processes, the sample is not cracked.

According to a sixty-seventh aspect, the radiopaque material of the sixty-sixth aspect or any other aspect, wherein, after subjecting the sample to the curing and steam autoclaving processes, the sample includes a non-breaking surface.

According to a sixty-eighth aspect, the radiopaque material of the sixty-seventh aspect or any other aspect, wherein, after subjecting the sample to the curing and steam autoclaving processes, the sample is substantially free of surface defects.

BRIEF DESCRIPTION OF THE FIGURES

FIG. 8 is a screenshot of an exemplary custom device design service, according to one embodiment of the present disclosure.

FIG. 10 is a screenshot of an exemplary custom device design service, according to one embodiment of the present disclosure.

DETAILED DESCRIPTION

Figure 1A:
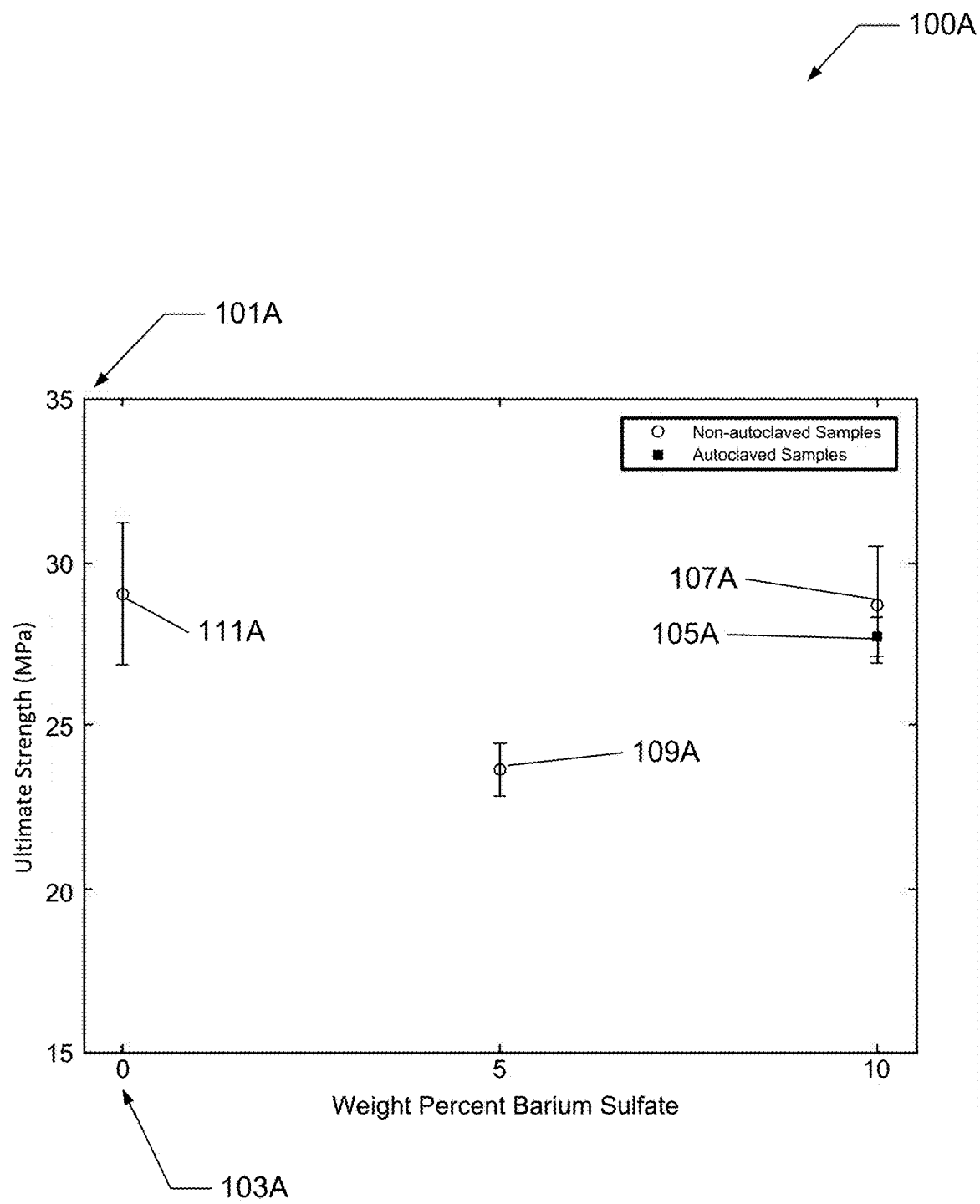
FIGS. 1A-B are charts illustrating mechanical performance of a custom device, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview of Custom Devices and Methods for Making Same

In one or more embodiments, the present devices may be formed using additive manufacturing technologies. In at least one embodiment, the present devices may be formed from a photo-curable resin and using a stereolithographic printing process. For example, the present devices may be formed from a polymer-based resin. In the same example, prior to doping (as described herein), the polymer-based resin may demonstrate exemplary properties including, but not limited to, properties listed in Table 1.

TABLE 1

Exemplary Resin Properties

|  | Pre-Cure | Post-Cure |
|---|---|---|
| Ultimate Tensile Strength | 12.0-23.0 MPa | 26.0-37.0 MPa |
| Tensile Modulus | 0.2-0.8 GPa | 0.9-1.5 GPa |
| Elongation | 60-75% | 40-55% |
| Flexural Stress at 5% Strain | 2.0-8.0 MPa | 20.0-35.0 MPa |
| Flexural Modulus | 0.1-0.5 GPa | 0.6-1.1 GPa |
| Notched IZOD | 125.0-135.0 J/m | 104.0-114.0 J/m |
| Heat Deflection Temp. | <35 degrees Celsius | 38.0-48.0 degrees Celsius |
| Thermal Expansion | 112.0-122.0 µm/m/degree Celsius | 140.0-150.0 µm/m/degree Celsius |

In various embodiments, the present devices may include features including, but not limited to, customized text and/or symbols, customized dimensions (e.g., associated with a specific patient and/or surgeon), radiopaque properties and/or increased mechanical resilience (as described herein).

In one embodiment, the present devices may withstand and recover from forces, torques and impulses typically experienced in a surgical setting (e.g., during an associated surgical procedure). In various embodiments, the present devices may demonstrate an increase in ultimate strength and bending yield strength in response to being treated in an autoclave (e.g., for sterilization purposes). Thus, in at least one embodiment, the present devices may become more resilient following autoclaving. In one or more embodiments, autoclaving may include, but is not limited to, dry heat autoclaving, steam autoclaving, other autoclaving techniques, and combinations of autoclaving techniques.

In various embodiments, the present devices may present mechanical properties rendering the devices sufficient for use in a surgical setting. FIGS. 1-2 provide data describing mechanical properties of custom devices, according to one embodiment of the present disclosure. Accordingly, the data provided herein is exemplary in nature and variations in mechanical properties are contemplated and may be achieved without departing from the scope and spirit of the present disclosure. Furthermore, the data provided herein may be considered independently from a particular resin utilized to produce prints (from which the data was sourced). Thus, the data provided herein may describe mechanical performance of any custom device fabricated using any resin suitable for additive manufacturing processes.

The exemplary data provided herein may be obtained via testing custom device samples according to one or more mechanical testing protocols (for example, a tensile testing protocol and a three-point bending protocol).

In at least one embodiment, a tensile testing protocol can include, but is not limited: 1) configuring a custom device sample of a particular shape (for example, an angular, dog bone shape) within a test system (for example a servohydraulic test system); 2) applying one or more known forces (e.g., tensile forces) to the sample; and 3) obtaining one or more strength and/or elongation metrics (for example, an ultimate tensile strength, tensile yield strength, failure displacement, etc.). In one or more embodiments, obtaining the one or more strength and/or elongation metrics can include, but is not limited to: 1) measuring one or more sample device dimensions (e.g., length, width, area, etc.) prior to, during, and/or after application of the one or more stresses; and 2) based on the one or more dimension measurements and the one or more known applied forces, calculating the one or more strength and/or elongation metrics.

In various embodiments, a three-point bending protocol can include, but is not limited to: 1) configuring a custom device sample of a particular shape (for example, an angular, dog bone shape) within a test system (for example a servohydraulic test system); 2) applying one or more force of known magnitude to a particular portion of the sample (for example, a portion of minimum cross-sectional area); and 3) obtaining one or more strength and/or elongation metrics (for example, an ultimate bending strength, bending yield strength, deflection distance, etc.). In at least one embodiment, the three-point bending protocol can include positioning the sample across a support span of known length (for example, about 122 or 128 mm). In various embodiments, the span length may be selected according to one or more calculations based on dimensions of the sample. In one or more embodiments, obtaining the one or more strength and/or elongation metrics can include, but is not limited to: 1) measuring one or more sample device dimensions (e.g., length, width, area, etc.) prior to, during, and/or after application of the one or more stresses; and 2) based on the one or more dimension measurements and the one or more known applied forces, calculating the one or more strength and/or elongation metrics.

As will be understood from discussions herein, apparatuses may be custom or standard devices (e.g., non-custom, batch, or mass produced). For example, the mechanical performance characteristics discussed in regards to FIG. 1A (or any other figure) may be for a standard device (e.g., a device of a standard or previously-known size/shape) that includes the features discussed herein (e.g., created via a photo-curable polymer). The term "custom device" as used herein does not exclude standard, non-custom, or mass-produced devices.

FIG. 1A illustrates a chart 100A that describes mechanical performance of custom devices (as described herein) under tension, according to one embodiment. In at least one embodiment, the custom devices described by the chart 100A may include one or more samples. In various embodiments, the one or more samples may be created according to one or more additive manufacturing methods described herein. For example, the one or more samples may be created according to a stereolithography technique, and the one or more samples may be subjected to curing treatments described herein.

The chart 100A relates ultimate tensile strength 101A to weight percent of barium sulfate (% $BaSO_4$) 103A. Thus, in at least one embodiment, the chart 100A relates ultimate tensile strength 101A (of present custom devices) to a weight percent of barium sulfate 103A (e.g., a weight percent included in photo-curable polymer that formed the present custom devices). The chart 100A further demonstrates a relationship between autoclaving a device and ultimate strength 101A. As shown in FIG. 1A, the chart 100A shows an autoclaved 10% BaSO4 sample 105A, a non-autoclaved 10% BaSO4 sample 107A, a non-autoclaved 5% BaSO4 sample 109A and a non-autoclaved 0% BaSO4 sample 111A. In at least one embodiment, sample 105A and sample 107A (including 10% BaSO4) may demonstrate an ultimate tensile strength between about 26-32 MPa. In one or more embodiments, sample 109A (including 5% BaSO4) may demonstrate an ultimate tensile strength between about 29-31 MPa. In one embodiment, sample 111A (including 0% BaSO4) may demonstrate an ultimate tensile strength between about 26-32 MPa. Accordingly, in one or more embodiments, the present devices may present an ultimate tensile strength between about 26-32 MPa. In at least one embodiment, the chart 100A indicates that autoclaving does not significantly affect ultimate tensile strength of the present devices that include about 10% barium sulfate, because ultimate strength for samples 105A and 107B are not significantly different in magnitude.

Figure 1B:
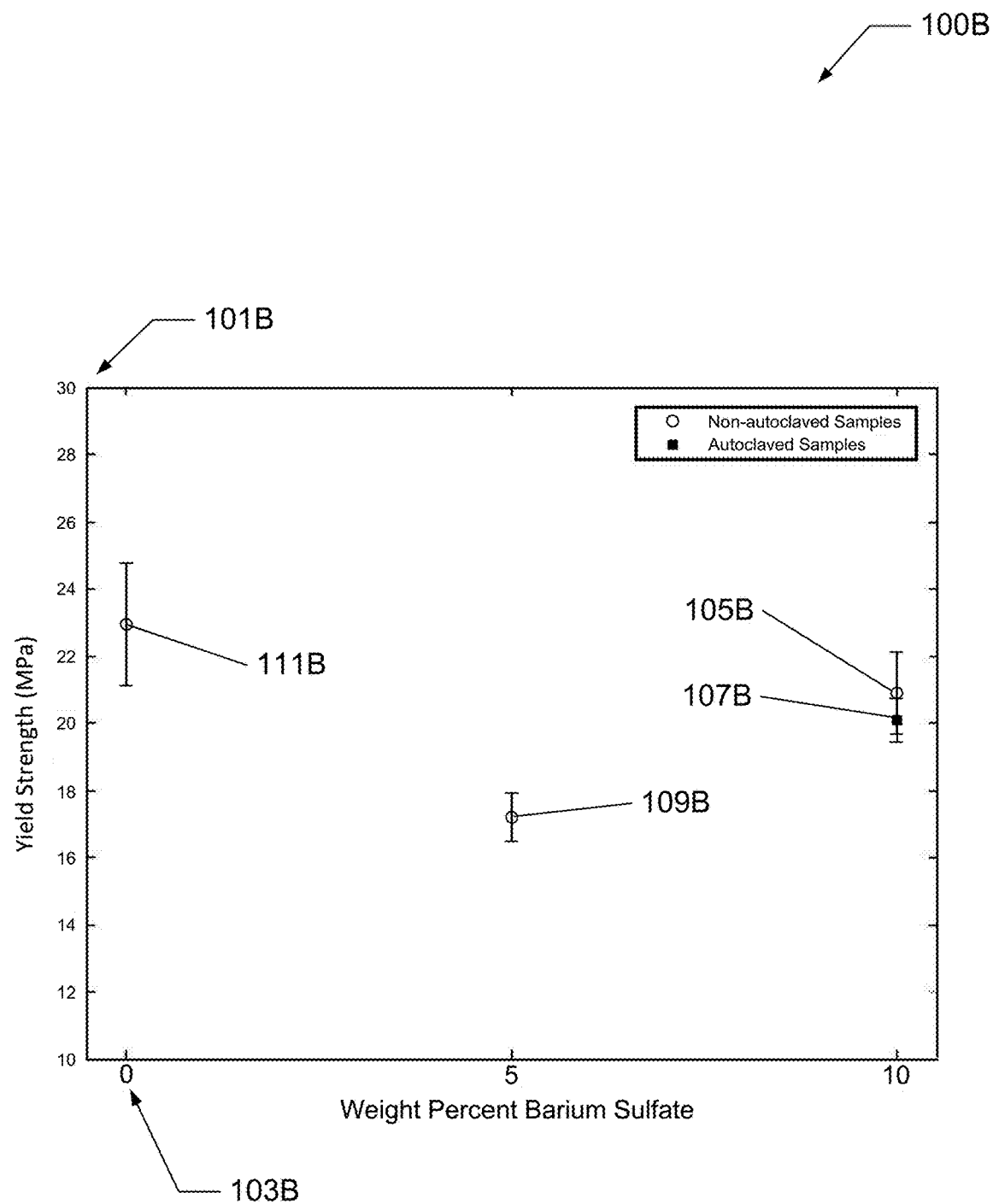

FIG. 1B illustrates a chart 100B that describes mechanical performance of custom devices (as described herein) under tension, according to one embodiment. In at least one embodiment, the custom devices described by the chart 100B may include one or more samples. In various embodiments, the one or more samples may be created according to one or more additive manufacturing methods described herein. For example, the one or more samples may be created according to a stereolithography technique, and the one or more samples may be subjected to curing treatments described herein.

The chart 100B relates yield strength 101B to weight percent of barium sulfate (% $BaSO_4$) 103B. In at least one embodiment, the chart 100B relates yield strength 101B (of present custom devices) to a weight percent of barium sulfate 103B (e.g., a weight percent included in photo-curable polymer that formed the present custom devices). The chart 100B further shows a relationship between autoclaving a device and yield strength 101B. The chart 100B includes an autoclaved 10% BaSO4 sample 105B, a non-autoclaved 10% BaSO4 sample 107B, a non-autoclaved 5% BaSO4 sample 109B and a non-autoclaved 0% BaSO4 sample 111B. In at least one embodiment, sample 105B and sample 107B indicate that the present devices (including 10% BaSO4) may demonstrate a yield strength between about 19-23 MPa. In one or more embodiments, sample 109B indicates that the present devices (including 5% BaSO4) may demonstrate a yield strength between about 20-25 MPa. In one embodiment, sample 111B indicates that the present devices (including 0% BaSO4) may demonstrate a yield strength between about 19-25 MPa. Accordingly, in one or more embodiments, the present devices may present a yield strength between about 16-25 MPa. In at least one embodiment, the chart 100B indicates that autoclaving does not significantly affect yield strength of the devices that include about 10% barium sulfate, because yield strengths of samples 105B and 107B are not significantly different in magnitude.

Figure 2A:
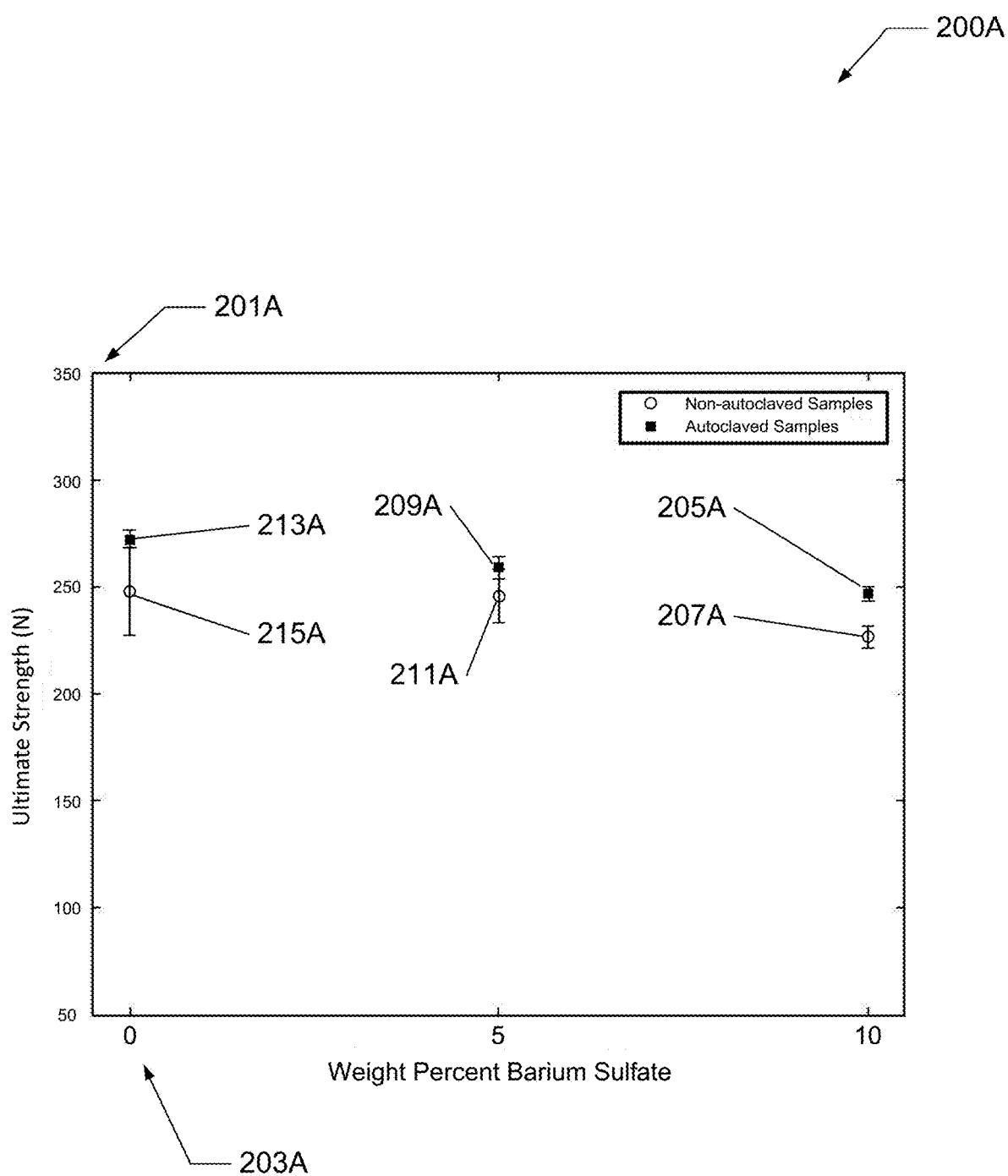
FIGS. 2A-B are charts illustrating mechanical performance of a custom device, according to one embodiment of the present disclosure.

FIG. 2A illustrates a chart 200A that describes mechanical performance of custom devices (as described herein) experiencing three-point bending, according to one embodiment. In at least one embodiment, the custom devices described by the chart 200A may include one or more samples. In various embodiments, the one or more samples may be created according to one or more additive manufacturing methods described herein. For example, the one or more samples may be created according to a stereolithography technique, and the one or more samples may be subjected to curing treatments as described herein. In at least one embodiment, the one or more samples may be subjected to three-point bending analyses. For example, the one or more samples may each be tested with a three-point bending test with a predefined support span (for example, about 128 mm). In the same example, the three-point bending test may be performed at a section of the sample that presents a minimum and/or minimal cross-sectional area.

The chart 200A relates ultimate strength 201A to weight percent of barium sulfate (% $BaSO_4$) 203A. As used herein, "ultimate strength" can refer to a metric calculated by dividing a particular measured force by an area (e.g., a minimum cross-sectional area). Thus, in at least one embodiment, the chart 200A relates ultimate strength 201A (of present custom devices) to a weight percent of barium sulfate 203A (e.g., a weight percent included in photo-curable polymer that forms the present custom devices). The chart 200A further shows a relationship between autoclaving a device and ultimate strength 201A. The chart 200A includes an autoclaved 10% BaSO4 sample 205A, a non-autoclaved 10% BaSO4 sample 207A, an autoclaved 5% BaSO4 sample 209A, a non-autoclaved 5% BaSO4 sample 211A, a non-autoclaved 0% BaSO4 sample 213A and a non-autoclaved 0% BaSO4 sample 215A.

In at least one embodiment, sample 205A and sample 207A indicate that the present devices (including 10% BaSO4) may demonstrate an ultimate strength between about 220-250 Newtons (N). In various embodiments, sample 209A and sample 211A indicate that the present devices (including 5% BaSO4) may demonstrate an ultimate strength between about 230-265 N. In one embodiment, sample 213A and 215A indicate that the present devices (including 0% BaSO4) may demonstrate an ultimate strength between about 220-280 N. Accordingly, in one or more embodiments, the present devices may present an ultimate strength between about 220-280 N. In at least one embodiment, the chart 200A indicates that autoclaving may increase ultimate strength of a custom device (described herein), because, in each pair of samples, the autoclaved sample demonstrated a higher ultimate strength compared to the corresponding non-autoclaved sample. In various embodiments, autoclaving a present device may increase an ultimate bending strength (of the device) by between about 4.0-14.0%. For example, autoclaving a present device may increase an ultimate bending strength by between about 4.0-10.0%, about 4.0-4.5%, about 4.5-5.0%, about 5.0-5.5%, about 5.5-6.0%, about 6.0-6.5%, about 6.5-7.0%, about 7.0-7.5%, about 7.5-8.0%, about 8.0-8.5%, about 8.5-9.0%, about 9.0-9.5%, about 9.5-10.0%, about 10.0-10.5%, about 10.5-11.0%, about 11.0-11.5%, about 11.5-12.0%, about 12.0-13.5%, about 13.5-14.0%, or about 14.0-14.5%.

Prior to experimentation that yielded the chart 200A, the relationship between autoclaving and ultimate strength (of a device formed from the present materials and methods) was not expected to be directly proportional (in any degree). Prior to experiments disclosed herein, it was commonly understood that autoclaving polymer-based devices decreases ultimate and yield strengths thereof. For example, as described at pg. 135 of *Comprehensive Biomaterials, Volume 1* (incorporated herein by reference), autoclaving techniques are not suitable for use with polymers that demonstrate a low melting temperature (e.g., a melting temperature, or the like, that is less than an autoclaving temperature). In at least one embodiment, the present devices may include polymers that demonstrate a heat deflection temperature (e.g., which may be analogous to melting temperature in this context) measuring less than an autoclaving temperature. For example, the present devices may include a polymer-based resin that demonstrates a heat deflection temperature of 30 degrees Celsius, which is considerably less than an exemplary autoclaving temperature (for example, 132 degrees Celsius). Because exemplary autoclaving processes would include subjecting polymer-based resin to temperatures in excess of the heat deflection temperature, one of ordinary skill in the art would expect that autoclaving the present resin (e.g., the resin having been formed and cured as described herein) would result in material deformation due to internal stresses and strains precipitated by the autoclaving temperatures. This expectation of non-autoclavability of devices produced from a polymer-based resin may be further supported by FIG. 12 and additional descriptions herein.

One of ordinary skill in the art would further expect that the deforming effects caused by autoclaving the present resin would result in, at best, unaffected mechanical performance, or, at worst, decreased mechanical performance including, but not limited to, decreased ultimate strength and decreased yield strength. Accordingly, the observed increase (in chart 200A) of ultimate strength in response to autoclaving constitutes an unexpected result.

Figure 2B:
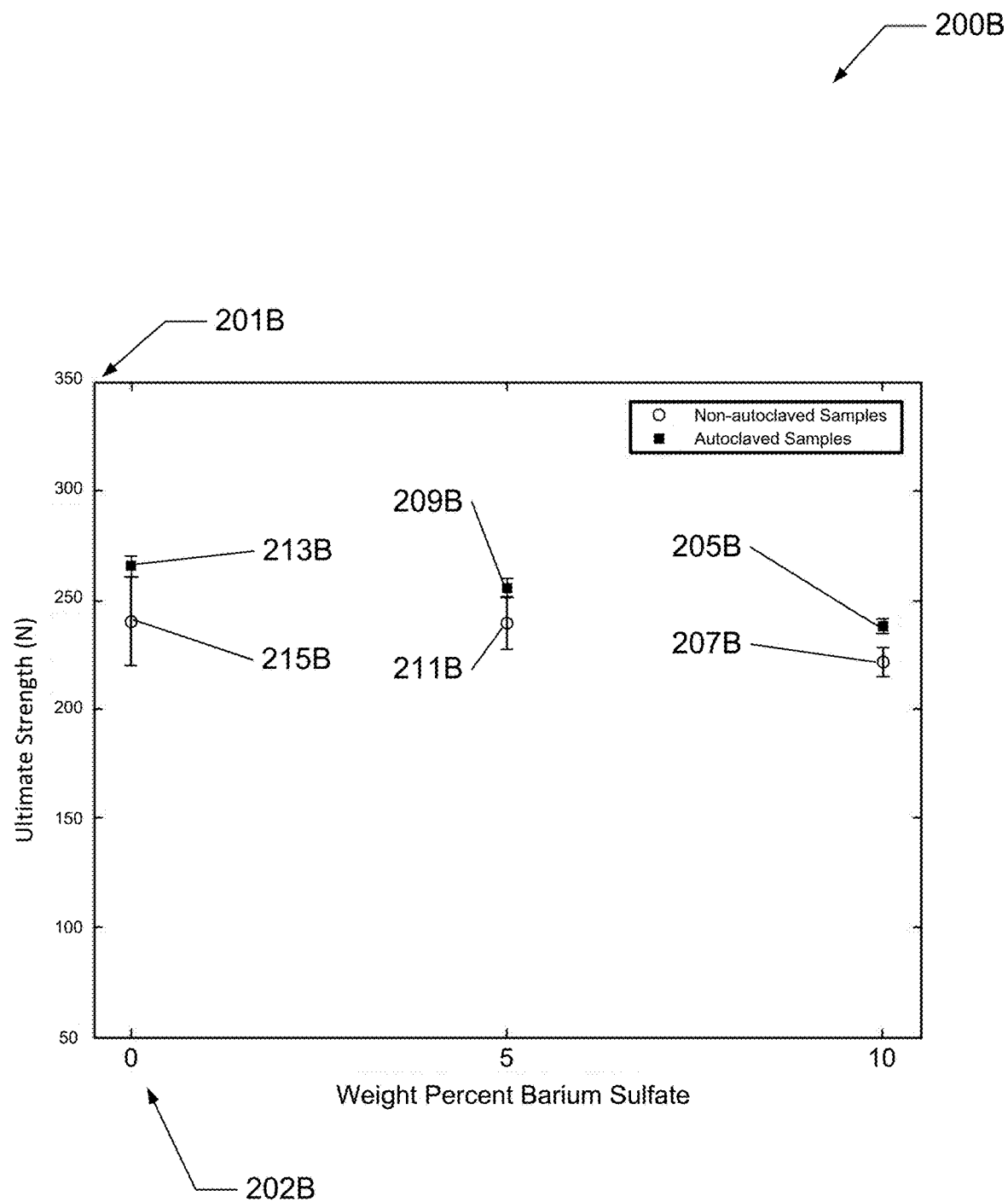

FIG. 2B illustrates a chart 200B that describes mechanical performance of custom devices (as described herein) experiencing three-point bending, according to one embodiment. In at least one embodiment, the custom devices described by the chart 200B may include one or more samples. In various embodiments, the one or more samples may be created according to one or more additive manufacturing methods described herein. For example, the one or more samples may be created according to a stereolithography technique, and the one or more samples may be subjected to curing treatments as described herein. In at least one embodiment, the one or more samples may be subjected to three-point bending analyses. For example, the one or more samples may each be tested with a three-point bending test with a predefined support span (for example, 128 mm). In the same example, the three-point bending test may be performed at a section of the sample that presents a minimum and/or minimal cross-sectional area. The chart 200B relates yield strength 201B to weight percent of barium sulfate (% BaSO$_4$) 203B. As used herein, "yield strength" can refer to a metric calculated by dividing a particular measured force by an area (e.g., a minimum cross-sectional area). In at least one embodiment, the chart 200B relates yield strength 201 (of present custom devices) to a weight percent of barium sulfate 203B (e.g., a weight percent included in photo-curable polymer that forms the present custom devices). The chart 200B further describes a relationship between autoclaving a device and resulting yield strength 201B. The chart 200B includes an autoclaved 10% BaSO4 sample 205B, a non-autoclaved 10% BaSO4 sample 207B, an autoclaved 5% BaSO4 sample 209B, a non-autoclaved 5% BaSO4 sample 211B, a non-autoclaved 0% BaSO4 sample 213B and a non-autoclaved 0% BaSO4 sample 215B. In at least one embodiment, sample 205B and sample 207B indicate that the present devices (including 10% BaSO4) may demonstrate a yield strength between about 210-245 N. In various embodiments, sample 209B and sample 211B indicate that the present devices (including 5% BaSO4) may demonstrate a yield strength between about 225-260 N. In one embodiment, sample 213B and sample 215B indicate that the present devices (including 0% BaSO4) may demonstrate a yield strength between about 220-270 N. Accordingly, in one or more embodiments, the present devices may present a yield strength between about 210-270 N.

In at least one embodiment, the chart 200B indicates that autoclaving may increase yield strength of a custom device (described herein), because, in each pair of samples, the autoclaved sample demonstrated a higher yield strength. In various embodiments, autoclaving a present device may increase an ultimate bending strength (of the device) by between about 2.0-15.0%. For example, autoclaving a present device may increase an ultimate bending strength by between about 5.0-9.0%, about 2.0-2.5%, about 2.5-3.0%, about 3.0-3.5%, about 3.5-4.0%, about 4.0-4.5%, about 4.5-5.0%, about 5.0-5.5%, about 5.5-6.0%, about 6.0-6.5%, about 6.5-7.0%, about 7.0-7.5%, about 7.5-8.0%, about 8.0-8.5%, about 8.5-9.0%, about 9.0-9.5%, about 9.5-10.0%, about 10.0-10.5%, about 10.5-11.0%, about 11.0-11.5%, about 11.5-12.0%, about 12.0-13.5%, about 13.5-14.0%, about 14.5-15.0%, or about 15.0-15.5%.

Prior to experimentation that yielded the chart 200B, the relationship between autoclaving and yield strength (of a device formed from the present materials and methods) was not expected to be directly proportional (in any degree). Accordingly, for similar reasons described herein regarding unexpected ultimate strength results, the observed increase (in chart 200B) of yield strength in response to autoclaving constitutes an unexpected result. As another example, prior to experiments described herein, it was not expected that adding a radiocontrast agent (e.g., barium sulfate) to a polymer would provide for device autoclavability (as described herein). Further, it was not expected that adding a radiocontrast agent would yield devices that, in response to being autoclaved, demonstrate increased ultimate strength and increased yield strength. For example, Design for Sterilization Part 1: Steam Sterilization (incorporated herein by reference and accessible at https://www.material-technology.com/single-post/2016/05/24/Design-for-Sterilization-part-1-Steam-Sterillization) describes that additives may be added to a plastic material to increase a heat deflection temperature. However, the reference does not describe using a radiocontrast agent as an additive, and, conversely, describes that combining additives with resins (used for surgical instruments) is unimportant. For this reason and other reasons described herein, it was unexpected that that adding a radiocontrast agent to a resin would result in devices (formed therefrom) with a combination of properties including radiopacity, autoclavability, and, upon being autoclaved, increased mechanical performance.

In at least one embodiment, the present devices may include integrally formed text and/or other characters. In various embodiments, the text and/or other characters may be formed during device fabrication and, thus, may appear on any surface of a fabricated device. Because the present devices may be formed via additive manufacturing, formation of the text and/or other characters may require no additional manufacturing steps, aside from steps taken to modify a digital design file (e.g., that is used to programmatically fabricate a device) in a manner such that the text and/or other characters are included in the design file. For example, a design file may be modified in a manner such that a top surface of an insertion device (e.g., to be fabricated via the present methods) includes text and an arrow character that directs a device user to properly orient the insertion device. Thus, in one or more embodiments, the present devices may include customized device orientation and/or operation instructions that are integrally formed with the devices and are located on one or more surfaces of the devices. In at least one embodiment, the text and/or other characters of the present devices may present a more economical solution to providing devices that include text and/or other character features. For example, previous solutions may produce text features by removing material from a device (e.g., laser etching, precision machining, etc.) until a text feature is formed in a negative space (e.g., from which the material was removed). Generation of text and other character features by removing material results in wasted material, thereby increasing material expense. In contrast, the present devices may waste significantly less material, because, by the present methods, no material is removed to form the text and other character features. Instead, the present methods, in at least one embodiment, utilize only as much material as is required to integrally form text and/or other character features with a device during manufacturing processes.

In some embodiments, text and/or other character features may be formed via material omission. Per the present disclosure, material omission refers to an additive manufacturing technique (for generating text and/or other character features) that includes establishing specific voids in a device during fabrication such that the voids form a text and/or other character feature. In one or more embodiments, material omission may produce (in a present device) text and/or other character features that may appear to be etched (e.g., by traditional methods), but instead were formed via inclusion of one or more voids (on one or more surfaces of the present device), thereby avoiding material waste associated with the traditional methods. Thus, the present methods may reduce material waste that is associated with forming text and/or other character features in a device, thereby potentially reduce material expenses for a device (e.g., in comparison to text/character-including devices fabricated from previous solutions).

Figure 3A:
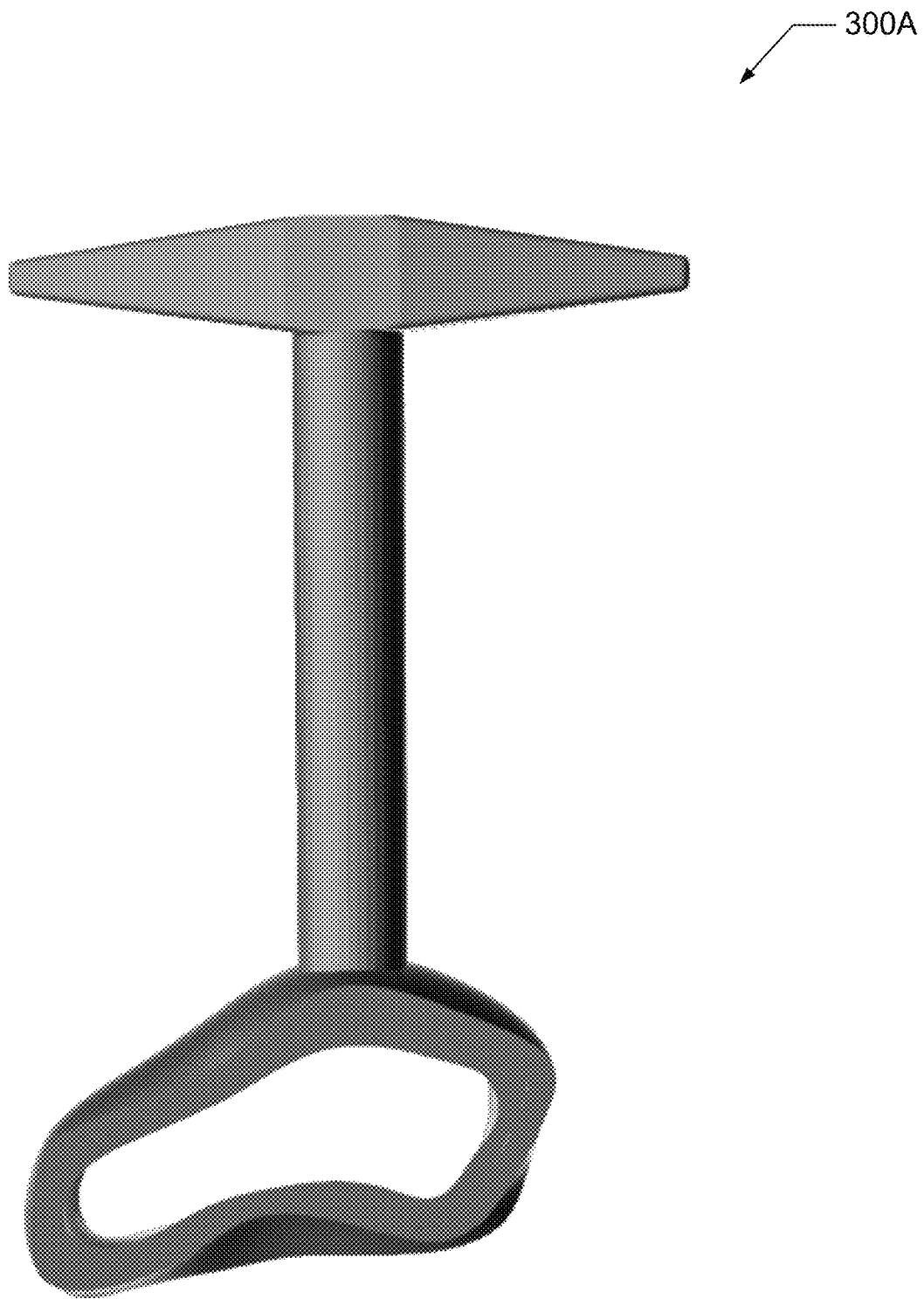
FIGS. 3A-C are exemplary custom devices with integrally formed text features, according to one embodiment of the present disclosure.
Figure 3B:
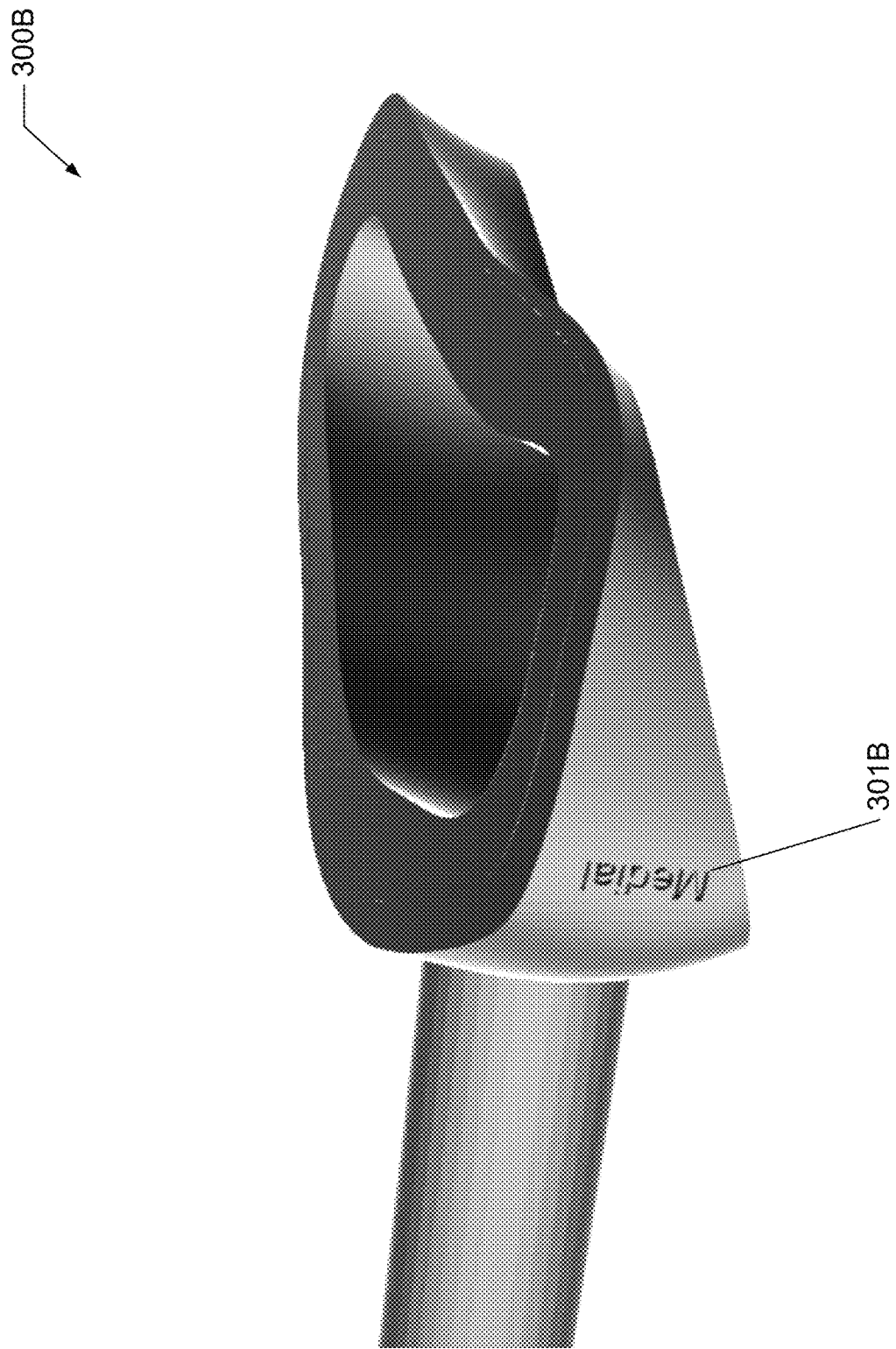

FIG. 3A illustrates a custom device 300A that may be produced via additive manufacturing methods described herein. FIG. 3B shows a partial view of custom device 300B (which may be the device illustrated in FIG. 3A) that includes a text feature 301B. In one or more embodiments, the text feature 301B may be integrally formed with the custom device 300B. In at least one embodiment, the text feature 301B may provide a user of the device 300B (for example, a surgeon) an orientation indication associated with use of the custom device 300B during a surgery. For example, the custom device 300B may be a trial for a custom foot wedge. In the same example, the text feature 301B may indicate to a surgeon (using the custom device 300B) that a region of the wedge (e.g., that would be disposed within the custom device 300B) should be oriented towards a medial area of a patient's foot (e.g., a foot of a patient undergoing implantation of the wedge). Thus, in at least one embodiment, a custom device may include one or more text and/or random character features that: 1) are integrally formed with the custom device; and 2) provide direction and/or an indication that is relevant to successful implementation of the custom device during a procedure.

Figure 3C:
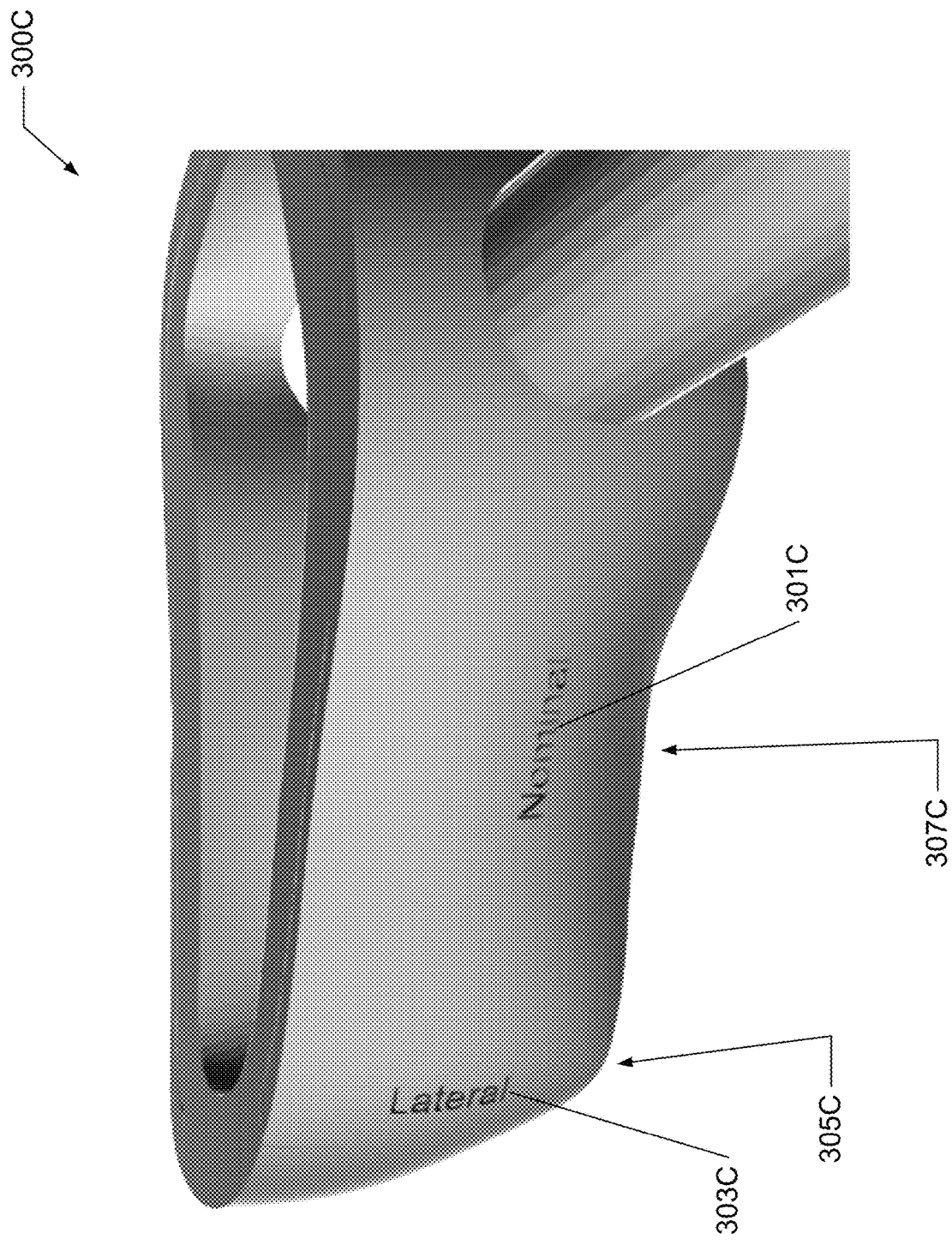

FIG. 3C shows a partial view of a custom device 300C (which may be the custom device illustrated in FIGS. 3A-B) that includes a first text feature 301C (custom device sizing information) and a second text feature 303C (custom device orientation information). In at least one embodiment, a custom device may include multiple text and/or other character features. In various embodiments, each of the multiple text and/or other character features may be integrally formed with any surface and/or region of the custom device. For example, it is noted that the first text feature 301C is integrally formed with a first surface 305C and the second text feature 303C is integrally formed with a second surface 307C. Thus, in one or more embodiments, a custom device (as described herein) may include any text and/or character feature on any surface and/or region of the custom device. In at least one embodiment, the text feature 301C may provide a user of the device 300C (for example, a surgeon) sizing information associated with use of the custom device 300C during a surgery. For example, the custom device 300C may be a trial for a custom foot wedge where the text indicates the size (for example, "nominal" as illustrated in text feature 301C) to provide guidance on which size device to implant into the patient.

In at least one embodiment, the present devices may be disposable. In various embodiments, the present devices may be sterilizable by one or more conventional methods typically employed for achieving sterilization in medical devices and instruments. In one or more embodiments, the present devices may be sterilized by methods including, but not limited to, steam treatment (e.g., autoclaving, or the like), radiation exposure, dry heat treatment, or chemical treatment (for example, ethylene oxide treatment). In at least one embodiment, the present devices may demonstrate in increase in one or more mechanical properties in response to being sterilized in an autoclave. For example, the present devices, following autoclaving, may demonstrate increased ultimate strength and yield strength (e.g., in comparison to strengths demonstrated by the devices prior to autoclaving).

In one or more embodiments, the present devices may include a handle element. In various embodiments, the handle element may be integrally formed with a device in a manner such that a user (e.g., a surgeon) may comfortably manipulate and orient the device (e.g., an instrument) and an attached device (e.g., an implant during an operation or procedure). In at least one embodiment, across versions of the present devices, the handle element may be substantially similar in structure and dimension. In at least one embodiment, the present devices may each be of an overall customized structure and form, but may each include a standardized handle element. In one embodiment, a standardized handle may reduce a number of device elements that require customized designs, thereby reducing complexity and, potentially, design costs associated with producing one or more devices (according to the present methods). For example, the present devices may all include a standard and generally cylindrical handle that includes structural and shape features that are ergonomic and/or textured to improve grip and ease device manipulation.

In various embodiments, the present devices may be formed from a photo-curable polymer. In one or more embodiments, the polymer may be doped with an imaging contrast agent (e.g., as described herein). In at least one embodiment, the imaging contrast agent results in devices (produced from the doped polymer) that are radiopaque.

In various embodiments, an imaging contrast agent may be integrally and homogenously combined (e.g., doped and mixed) into a resin (e.g., a photo-polymeric resin utilized in 3D printing). In at least one embodiment, a suitable imaging contrast agent may be barium sulfate.

Figure 4:
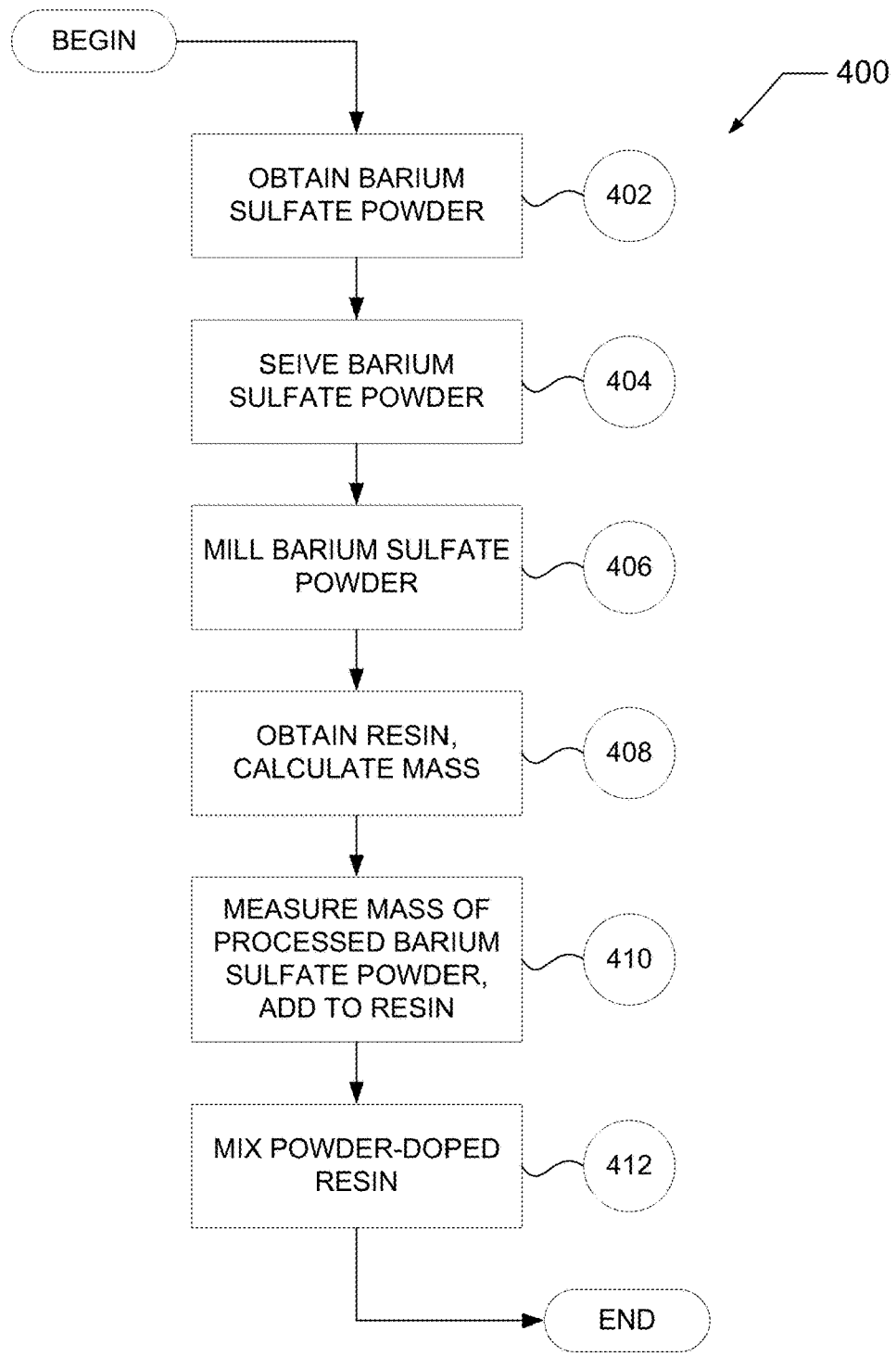
FIG. 4 is a flowchart illustrating an exemplary process for creating a doped resin mixture according to one embodiment of the present disclosure.

FIG. 4 is a flowchart illustrating an exemplary process for creating a doped resin mixture according to one embodiment. As will be understood by a person having ordinary skill in the art, the steps and process show in FIG. 4 (and those of all other flowcharts and sequence diagrams shown and described herein) may operate concurrently and continuously, are generally asynchronous and independent, and are not necessarily performed in the order shown. In various embodiments, one or more steps and processes shown in FIG. 4 (and those of all other flowcharts and sequence diagrams shown and described herein) may be performed with repetition or may be omitted.

At step 402, a manufacturer (e.g., a performer of the present methods) obtains barium sulfate in a powdered form, which may include one or more particles sizes.

At step 404, the manufacturer sieves the barium sulfate powder to isolate a particular particle size. In one or more embodiments, a smaller particle size may produce a more suitable doped resin, thus resulting in more suitable and/or successful printing products (e.g., polymer-based radiopaque devices of the present technology).

At step 406, the manufacturer processes the barium sulfate powder in a milling machine (e.g., a ball mill) for the purposes of decreasing and standardizing particle size. In one or more embodiments, sieving and milling may occur in any combination and/or repetition to obtain a desired particle size. In at least one embodiment, barium sulfate powder may only be subject to sieving or may only be subject to milling. In various embodiments, barium sulfate powder, which has been subject to sieving and/or milling, may be referred to as processed barium sulfate powder.

In one or more embodiments, the manufacturer may optimize a particle size of the barium sulfate powder to obtain desired viscosity and/or resin consistency for optimal printability and product (e.g., polymer-based radiopaque device) properties. In at least one embodiment, inappropriate imaging contrast agent particle size may result in printing failures and/or printed products (e.g., polymer-based radiopaque devices) exhibiting defects including, but not limited to: 1) rough surface finish; 2) uneven imaging signature; and 3) lower mechanical properties. In various embodiments, a finer processed barium sulfate powder particle size may result in a more homogenous distribution of the processed barium sulfate powder throughout a resin mixture (e.g., produced according to one or more methods further described herein).

In various embodiments, a resin of the present disclosure refers to a photo-polymeric resin. One of ordinary skill in the art will recognize photo-polymeric resin refers to a polymer that changes properties when exposed to light.

At step 408, the manufacturer obtains resin and calculates a given mass of resin to be doped and mixed. In at least one embodiment, the manufacturer obtains resin and calculates a given mass by multiplying a volume of resin (e.g., 1 liter) by the specific gravity of the resin. In various embodiments, the manufacturer dispenses the volume of resin (e.g., from a cartridge) into a beaker and, if necessary, retains the cartridge (e.g., for additional processes described herein).

At step 410, the manufacturer weighs a specific mass of processed barium sulfate powder, from 1-10% (or more) weight percent of the resin, and adds the specific mass to the beaker containing the volume of resin, thus forming a resin mixture. In at least one embodiment, the specific mass of processed barium sulfate powder added to the volume of resin may depend on the given mass of resin calculated by the manufacturer and may depend on one or more properties required by a polymer-based radiopaque device produced according to the one or more present methods.

At step 412, the manufacturer mixes the resin mixture until there are no visible chunks of processed barium sulfate powder visible in the resin mixture, thereby forming a doped resin. In one or more embodiments, mixing may be performed with an electric mixer, or the like. In various embodiments, the manufacturer may conduct doping and mixing, as described above, on a larger batch scale (for example, 10 cartridges worth of resin and imaging contrast agent at once). In at least one embodiment, the manufacturer conducts batch scale-mixing of the resin mixture using an industrial-type mixer of suitable capacity. In one or more embodiments, the manufacturer pours (e.g., via a funnel) the doped resin back into the corresponding cartridge retained earlier in the process. In at least one embodiment, the retained cartridge may be modified (e.g., as described herein) prior to the manufacturer pouring the doped resin.

Figure 5:
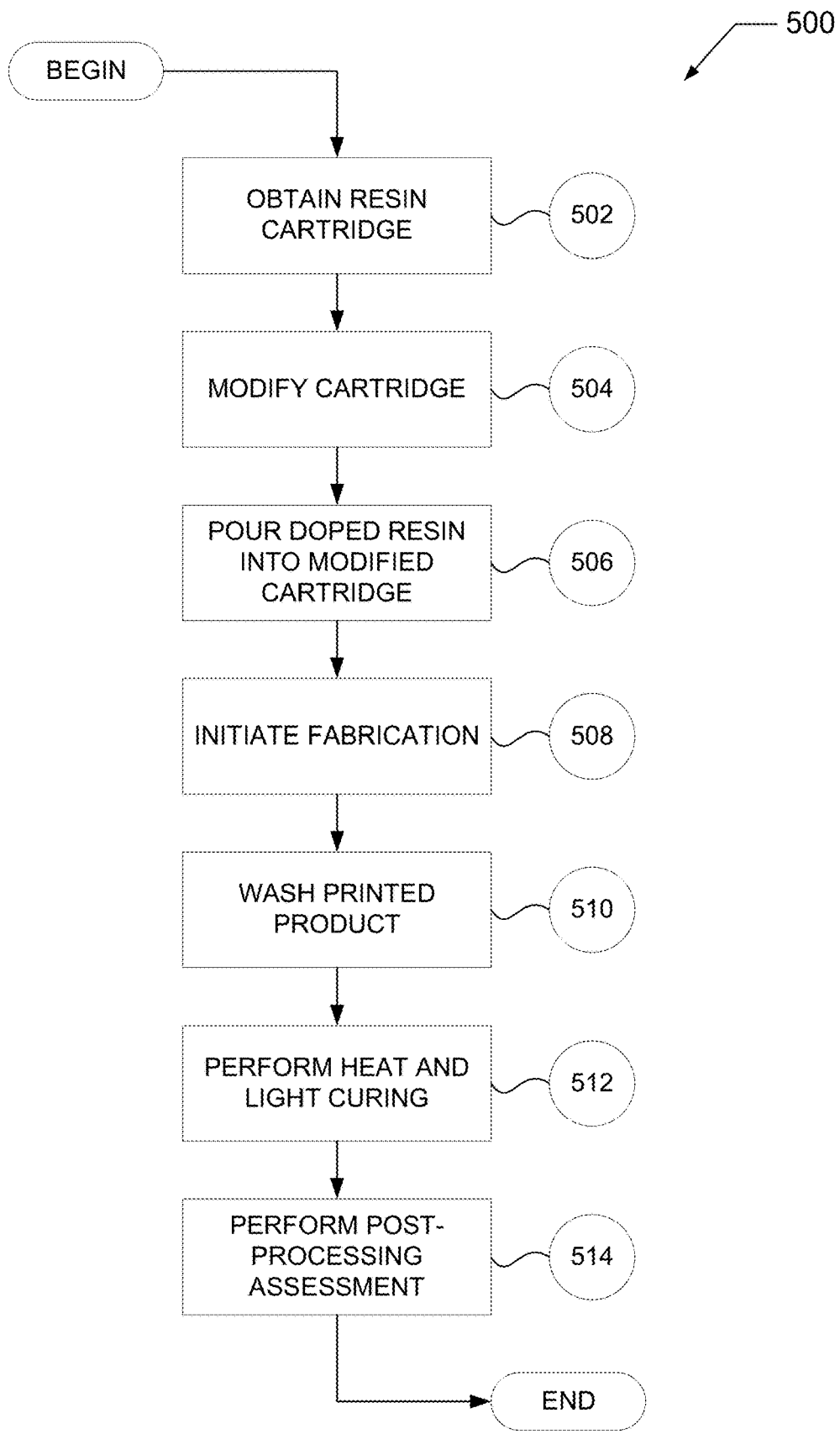
FIG. 5 is a flowchart illustrating an exemplary process for producing a custom device according to one embodiment of the present disclosure.

FIG. 5 is a flowchart illustrating an exemplary process for producing a custom device according to one embodiment. Recited herein are one or more parameters for a custom device production process. The present disclosure recites various magnitudes of curing parameters, the curing parameters including, but not limited to, temperature, wavelength and time variables. The recited curing parameter magnitudes are for illustrative purposes, and variations in curing parameter magnitudes may be effected without departing from the spirit and scope of the novel concepts of the disclosure. In various embodiments, custom devices of differing, similar or identical design, or of differing material, may include disparate parameters and parameter magnitudes for fabrication processes. For example, a first custom device may include a cure wavelength of 405 nm, a cure temperature of 75 degrees Celsius and a cure time of 45 minutes. In the same example, a second custom device may include a cure wavelength of 375 nm, a cure temperature of 55 degrees Celsius and a cure time of 75 minutes.

Furthermore, one of ordinary skill in the art will understand that additive manufacturing processes described herein (in particular, stereolithography 3D printing methods) may include light and/or heat curing treatments that occur during printing processes. One of ordinary skill in the art will further understand that, while such in-print curing treatments may occur during the present methods, curing treatments described herein may refer to a curing process that is distinct from any and all in-print curing treatments. For example, the present methods may include a 3D printing step performed on a stereolithography printer, and the stereolithography printer, during printing, may include a laser and a heating element that modify properties of a photo-curable resin via light treatment and heat treatment (e.g., such as heat exposure measuring 35 degrees Celsius). In the same example, the present methods may include a distinct curing step performed after printing that includes, but is not limited to, treating the photo-curable resin with light and/or heat curing treatments.

In various embodiments, modification of a cartridge may be required to compensate for an increase in a viscosity of the doped resin (e.g., as compared to un-doped resin). In one or more embodiments, the increase in the viscosity of the doped resin may cause (e.g., in unmodified cartridges) interrupted disposal of the doped resin during printing. In at least one embodiment, interrupted disposal of the doped resin during printing may result in printing failures and/or other printing abnormalities, whether in the printer itself or a resulting product of the printer (e.g., a polymer-based radiopaque device).

At step 502, a manufacturer obtains a resin cartridge. For example, the manufacturer may obtain a resin cartridge that was retained during a resin doping process (e.g., as is described herein and illustrated in FIG. 1). In at least one embodiment, the manufacturer may obtain any number of resin cartridges required to meet material demands for a device fabrication process.

At step 504, the manufacturer deepens an opening in an outlet of the obtained cartridge (e.g., a slit in the cartridge outlet) and creates an additional opening (e.g., an additional slit) in the cartridge outlet that is orthogonal to the opening. In at least one embodiment, cartridge modification processes may be performed automatically and/or manually. In at least one embodiment, the cartridge modification processes may include equipment that is configured to make necessary modifications to one or more cartridges in quick repetition and at scale. For example, cartridge modification may be performed in an assembly line fashion that quickly processes unmodified cartridges through at least one machine that performs modifications, described herein, on each unmodified cartridge. In at least one embodiment, modifications to a resin cartridge may compensate for increased viscosity of doped resin (e.g., to be poured into and, with emphasis, from the cartridge) by increasing a flow rate of the doped resin out of a cartridge outlet.

In one or more embodiments, a cartridge may be used that does not require modification. For example, an unmodified cartridge that is manufactured to compensate for a more viscous resin may be used. In at least one embodiment, an unmodified cartridge (of the present methods) may demonstrate a specific flow rate that is sufficient for supplying doped resin (as described herein) in suitable capacity to an additive manufacturing machine. Accordingly, in one or more embodiments, step 504 may be omitted, for example, in instances where cartridge compensation for viscosity of doped resin is not required.

At step 506, the manufacturer pours the doped resin into a cartridge (if required, a cartridge modified as described in step 504). In at least one embodiment, the manufacturer may further install the filled cartridge into an additive manufacturing machine. For example, the manufacturer may install the filled cartridge within a stereolithography ("SLA") 3D printer. In one or more embodiments, a 3D printer of the one or more present methods may include a wiper arm. In various embodiments, the wiper arm mixes the doped resin (e.g., in a reservoir and/or tray of the 3D printer) throughout printing processes.

At step 508, the manufacturer initiates fabrication. In various embodiments, fabrication may include, but is not limited to, forming, from a doped photo-curable resin mixture, a particular shape (e.g., a polymer-based radiopaque device). In at least one embodiment, forming the particular shape may include one or more additive manufacturing techniques (for example, SLA 3D printing). In one or more embodiments, the formed (e.g., printed) particular shape may be subjected to additional post-printing processes.

At step 510, the manufacturer washes the particular shape, including any and all composite components, in isopropyl alcohol (IPA) for a specific period of time (e.g., 10 minutes) to clean the particular shape and remove uncured resin. In at least one embodiment, the manufacturer conducts a curing process to optimize mechanical properties of the product.

At step 512, the manufacturer heats the particular shape to about 60 degrees Celsius for about 60 minutes. In one or more embodiments, the manufacturer bathes the particular shape in 405 nm light for the duration of heating. In at least one embodiment, a process of heating the product for a length of time (e.g., 60 minutes) while bathing the product in 405 nm light may be referred to as a "curing" process. In various embodiments, a product of the "curing" process may be a polymer-based radiopaque device.

At step 514, the manufacturer conducts a post-processing inspection of a product (produced from the particular shape via the "curing" process). In one or more embodiments, the post-processing inspection may include, but is not limited to: 1) dimensional verification, wherein the manufacturer ensures the product meets one or more engineering specifications and/or parameters; and 2) visual appearance, wherein the manufacturer ensures a surface finish and physiognomy of the product aligns with one or more design specifications and/or parameters. In at least one embodiment, the manufacturer may conduct the post-processing inspection following completion of the curing process described above.

In any embodiment herein, the manufacturer may include a person, one or more machines, or a combination of the person and the one or more machines. In various embodiments herein, the one or more present methods may be performed (e.g., by the manufacturer) automatically and/or manually.

Description of Additional Systems and Methods for Generating a Custom Design

In various embodiments, the present devices may be created, in part, via one or more software-based techniques. In at least one embodiment, device designs (e.g., that are used in additive manufacturing processes described herein) may be automatically and/or manually edited via computer programs, software, or the like, that run algorithmic processes to facilitate customization of device designs. In at least one embodiment, one or more software-based techniques may be performed as described in U.S. patent application Ser. No. 15/910,549, now U.S. Pat. No. 10,183,442, filed Mar. 2, 2018, entitled "MEDICAL DEVICES AND METHODS FOR PRODUCING THE SAME," which is incorporated by reference herein, in its entirety.

In at least one embodiment, one or more dimensions of the present devices may be automatically computed via at least one computer running one or more software programs. In one or more embodiments, the one or more software programs may utilize a variety of inputs including, but not limited to: 1) patient imaging data (including x-rays, scans, MRI images, etc.); and 2) anonymized patient medical data (for example, weight, height, etc.). In various embodiments, the one or more software programs may receive a command (e.g., from a server, from a computer input tool, such as a keyboard, etc.) that includes the variety of inputs, as well as additional data regarding a device design (for example, a device identifier, etc.). In various embodiments, upon executing the command, the one or more software programs may automatically generate a custom device design based on received patient metrics and other information.

In at least one embodiment, the one or more software programs may generate a partial device design. For example, the one or more software programs may generate a design for a handle component and a shaft component of a custom insertion device. In the same example, the one or more software programs may base a length and width of each component on patient imaging data that, when analyzed algorithmically, provide dimensions of patient anatomy. In various embodiments, the one or more software programs may retrieve, from memory, a design template that serves as a foundational design of a custom device. In at least one embodiment, the template may be sourced from a previous custom device design and/or from a device design associated with an approved medical device (for example a 510(k)-approved device). In one or more embodiments, the one or more software programs may analyze uploaded patient image data to extract one or more template modification metrics and modify a retrieved design template to be properly dimensioned with respect to the extracted one or more metrics. Thus, in at least one embodiment, present devices may be partially or fully designed using one or more software programs that receive various inputs and execute one or more algorithmic processes to automatically generate custom device designs.

In various embodiments, the one or more software programs may receive Digital Imaging and Communications in Medicine ("DICOM") images that may be medical imagery of a patient. In particular, the DICOM images may be images of an area of a patient where a procedure may occur (for example, a vertebra implant site). In at least one embodiment, the DICOM images may be sourced from a variety of medical imaging techniques including, but not limited to: 1) X-Ray; 2) computed tomography (CT); 3) magnetic resonance imaging (MRI); and 4) other medical imaging modes. In one or more embodiments, the one or more software programs may execute algorithmic functions and/or protocols that analyze and extract metrics from the DICOM images.

For example, the one or more software programs may receive anonymized patient information and DICOM images (e.g., X-rays) of a patient scheduled to receive a cervical cage implant. In the same example, the one or more software programs may analyze the images of the patient to collect metrics and dimensions of the patient's spinal column. Continuing the example, from the metrics, dimensions and other inputs (e.g., a device identifier), the one or more software programs may generate an electronic design file for a cervical cage inserter that includes a shaft with a customized length and width sourced from algorithms that optimize cervical inserter dimensions for best performance during a procedure. In at least one embodiment, the electronic design file may be automatically and/or manually transmitted to at least one additive manufacturing device (e.g., equipment, a printer, etc.). In one or more embodiments, the at least one additive manufacturing device may automatically process the received electronic design file and print one or more of the cervical cage and/or cervical cage inserter (e.g., as described herein).

Figure 6:
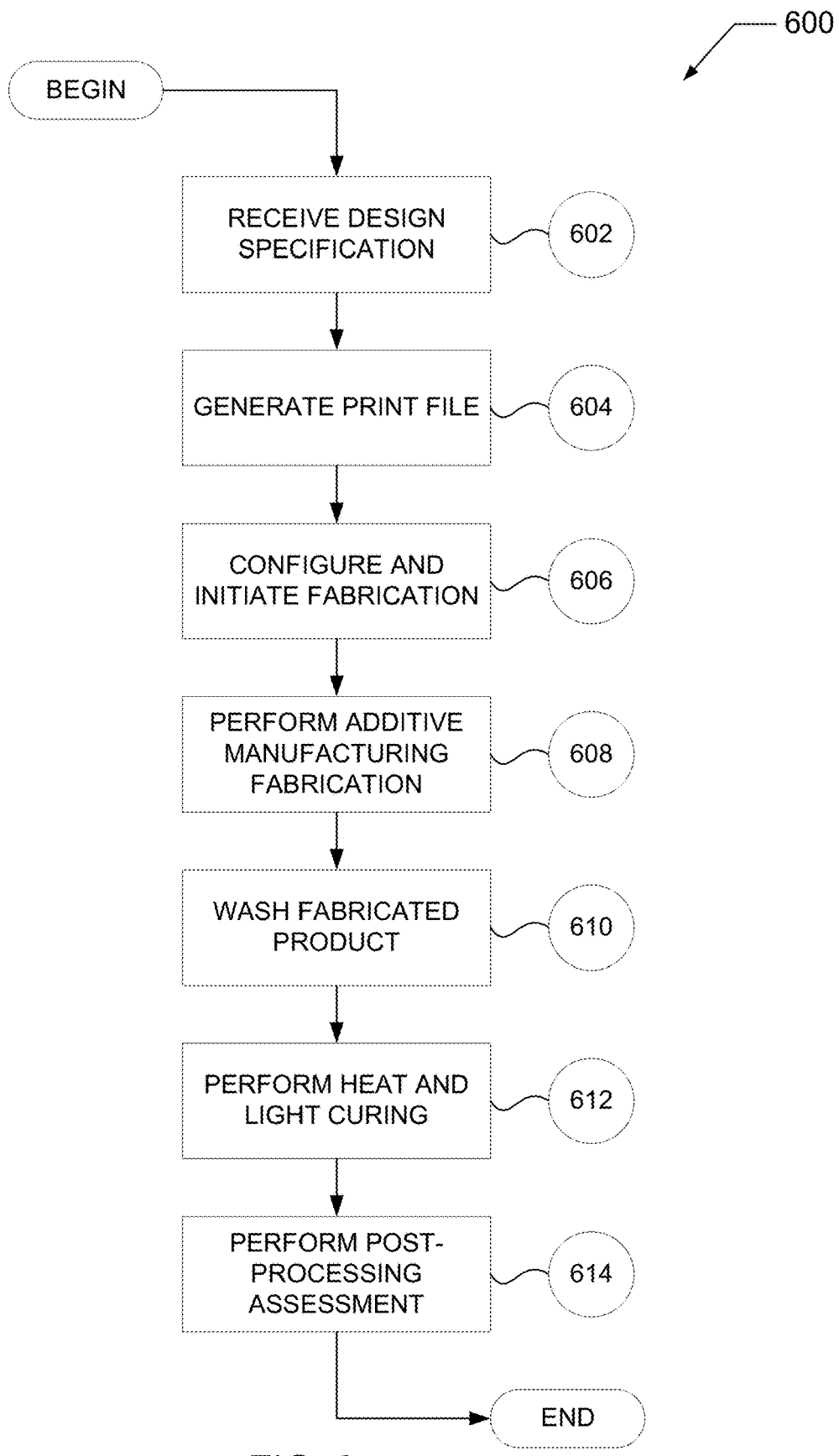
FIG. 6 is a flowchart illustrating an exemplary process for producing a custom device according to one embodiment of the present disclosure.

FIG. 6 is a flowchart illustrating an exemplary process for producing a custom device according to one embodiment.

At step 602, a design specification is received at a server. In various embodiments, the design specification may be received at any suitable computing environment. In one or more embodiments, the design specification may include, but is not limited to: 1) device design information (e.g., procedure, scheduling information, device identifier, etc.); 2) anonymized patient information (e.g., DICOM imagery, diagnosis, dimensions, etc.); and 3) requestor information (e.g., information regarding a source that requested design and fabrication of a device). A design specification may include any and all information required to generate a custom electronic design file for a surgical device. In at least one embodiment, the server provides the design specification to at least one processor that parses the design specification, organizes and stores (in memory) all information included therein.

At step 604, the at least one processor generates a print file. In at least one embodiment, the print file may be formatted such that additive manufacturing equipment (for example, an SLA printer) may immediately fabricate one or more devices based on the print file. In one or more embodiments, the at least one processor may generate and/or identify and retrieve a generic design template. In one embodiment, the generic design template may be associated with a device identifier included in the design specification. For example, the design specification may include a device identifier for a generic design template of a cervical cage inserter. In the same example, the at least one processor may automatically retrieve an electronic design file for the generic template and, based on the template, generate an initial print file.

In various embodiments, the at least one processor may perform one or more analyses of DICOM imagery received from the specification. In at least one embodiment, the at least one processor performs one or more algorithmic processes to analyze patient image data included in the design specification. Continuing with the same example, the at least one processor may analyze X-ray imagery of a patient and compute one or more metrics and/or dimensions of one or more elements of the initial print file. Thus, in various embodiments, the at least one processor may modify an initial print file based on the computed metrics and/or dimensions. Continuing with the above example, the at least one processor may: 1) identify a specific depth of the patient's spinal column (e.g., relative to skin surface); 2) calculate an optimal shaft length for the cervical cage inserter; and 3) revise the initial print file with the optimized shaft length. In at least one embodiment, objectives of optimization may include, but are not limited to: 1) reduction of patient risk during a procedure; 2) increase probability of procedure success; 3) increase comfort of surgeon during procedure; and 4) increase ease of manipulation and/or interaction of a device during a procedure.

In one or more embodiments, the at least one processor may modify the print file to include one or more text and/or character features (as described herein). In at least one embodiment, the at least one processor may provide the generated, optimized, and modified print file to the server.

At step 606, the server receives a print file from the at least one processor, configures and initiates a fabrication process (e.g., for fabricating a device based on the print file). In at least one embodiment, configuration of fabrication, via the server and at least one processor, may include determination and establishment of fabrication logistics. In various embodiments, fabrication logistics may include, but are not limited to: 1) fabrication scheduling (e.g., fabrication start and end dates); 2) fabrication materials (e.g., material type(s) and quantity(ies) required); 3) fabrication settings (e.g., resolution, etc.); and 4) other logistical determinations. In one or more embodiments, the server may communicate with at least one processor to determine and establish (e.g., in an electronic database, in equipment programming, etc.) fabrication logistics. In various embodiments, to configure fabrication, the server and/or the at least one processor may retrieve and utilize logistics-related information from one or more sources including, but not limited to: 1) inventory management systems; 2) scheduling systems; 3) memory; and 4) at least one data historian.

In various embodiments, the server and the at least one processor may determine a specific time at which fabrication of a device (e.g., via additive manufacturing equipment) may commence. In at least one embodiment, the server and at least one processor may utilize, individually or in combination, a procedure date, a manufacturing duration and one or more additional temporal variables to determine the specific time of fabrication commencement. In one or more embodiments, the server and the at least one processor may leverage inventory management systems to determine if sufficient fabrication materials are in stock (and, if not in stock, determine an estimated material delivery time) and, accordingly, may adjust the specific time based on the determination (for example, the specific time may be delayed based on estimated times for material shipments, etc.).

In various embodiments, upon conclusion of fabrication configuration, the server and the at least one processor may execute fabrication initiation. In one or more embodiments, fabrication initiation may include, but is not limited to: 1) recording fabrication configuration information in memory (e.g., and/or in a database, data historian, etc.); 2) transmitting a fabrication command to a fabrication manager (which may be a computer, a software program and/or a machine operator) and/or directly to additive manufacturing equipment; and 3) generating and transmitting a fabrication initialization report to a device manufacturer, device user (e.g., an entity that requested and/or provided a design specification) and/or an electronic record system. In at least one embodiment, a fabrication command may include, but is not limited to: 1) a print file; 2) a quantity of devices to be fabricated based on the print file; 3) at least one fabrication time variable (for example, the specific time at which fabrication may commence); and 4) other logistical information associated with organizing and tracking print files and devices. In at least one embodiment, the server may communicate with additive manufacturing equipment (and/or a controller thereof) to initiate a logistically metered fabrication process, the output of which is one or more custom devices.

At step 608, additive manufacturing equipment receives a fabrication command (e.g., from the server, a fabrication manager, etc.) and performs additive manufacturing fabrication operations to produce one or more custom devices based on a received print file. In at least one embodiment, the additive manufacturing equipment, and one or more operators thereof, may perform one or more additive manufacturing techniques described herein. For example, the additive manufacturing equipment may include at least one SLA 3D printer that utilizes a photo-curable polymer. In the same example, the photo-curable polymer may be a doped resin as described herein, thereby resulting in one or more printed devices being radiopaque. In at least one embodiment, the additive manufacturing equipment may utilize modified resin cartridges (as described herein) that contain doped resin.

In various embodiments, the additive manufacturing equipment (in particular, one or more SLA 3D printers) may include at least one component configured to improve printing resolution and reduce printing errors. In at least one embodiment, the additive manufacturing equipment may include a wiper arm that mixes resin throughout printing processes. In some embodiments, the wiper arm makes uniform an SLA printing reservoir surface at regular intervals (for example, after each layer is printed). In one or more embodiments, a speed and or frequency of the wiper arm may be configured programmatically (e.g., to compensate for variations in resin viscosity, etc.).

In one or more embodiments, the additive manufacturing equipment proceeds with fabrication of the one or more devices until a predefined device quantity has been reached. In at least one embodiment, fabrication may occur on a rolling basis. For example, a newly fabricated device may be removed and submitted to additional steps (described herein) while the additive manufacturing equipment (from which the device was removed) proceeds with fabricating additional devices.

At step 610, a fabricated device is washed. In at least one embodiment, the wash may include an organic solvent at a specific concentration. In at least one embodiment, the organic solvent is isopropyl alcohol and the specific concentration may be between about 5-99% (v/v). In various embodiments, washing of a fabricated device may proceed for a predetermined time interval (for example, 10 minutes). In some embodiments, washing may be repeated (for example, washing may occur in 3-5 repetitions, each occurring for a predetermined interval). In one or more embodiments, washing of a fabricated device may be performed on an individual device basis, or may be performed en masse (e.g., with a plurality of fabricated devices). In various embodiments, washing may be performed automatically (e.g., by one or more machines in an assembly fashion) or may be performed manually.

At step 612, one or more fabricated devices are subjected to a heat and light curing treatment. In at least one embodiment, the treatment cures the polymer (or resin) from which the one or more fabricated devices were formed. In various embodiments, curing refers to instigating a chemical and/or physical process that cross-links chains in a polymer, thereby resulting in a hardened and/or toughened material. In at least one embodiment, the one or more fabricated devices are subjected to heat and light curing to finalize fabrication and produce one or more cured devices with desired mechanical properties (e.g., a specific hardness, etc.).

In one or more embodiments, heat curing may include heating the one or more fabricated devices to a predetermined temperature for a predetermined time interval. In at least one embodiment, the predetermined temperature may be about 60 degrees Celsius and the predetermined time interval may be about 60 minutes. In various embodiments, the predetermined temperature and predetermined time interval may be adjusted, individually or in combination, to produce optimal curing effects for a fabricated device formed from a specific polymer. For example, the predetermined temperature and predetermined time interval may be increased in response to a fabricated device being composed of a polymer with a cure temperature of 85 degrees Celsius and a cure time of 90 minutes.

In one or more embodiments, light curing may include bathing the one or more fabricated devices with a light of a predetermined wavelength and intensity for a predefined time interval. In at least one embodiment, the predetermined wavelength and predetermined intensity may be selected to be sufficient for producing curing effects at any depth within the one or more fabricated devices (e.g., and within the predefined length of time). In various embodiments, the predetermined wavelength may be about 405 nm and the predefined time interval may be about 60 minutes. In at least one embodiment, heat curing and light curing may occur simultaneously, and may be suspended individually upon reaching a respective predefined time variable.

At step 614, a post-processing assessment is performed on one or more cured devices. In at least one embodiment, the post-processing assessment may include, but is not limited to: 1) mechanical performance testing; 2) device integrity testing; 3) contamination and toxicity testing; 4) imaging testing (for example, to confirm radiopaque properties); and 5) visual inspection. In one or more embodiments, the one or more cured devices may be subjected to additional machining and/or finalization processes. In various embodiments, an output of the post-processing assessment may be one or more custom devices for use in a surgical setting. Thus, in one or more embodiments, the present disclosure provides custom surgical devices and one or more methods for producing the same (e.g., via additive manufacturing processes).

In at least one embodiment, a software application may be provided and utilized for producing a custom device. In one or more embodiments, the software application may include or be accessed by a website accessible via a network (for example, the Internet). In at least one embodiment, the software application may be operatively connected to or access memory and/or storage (for example, a distributed database, etc.) that stores and transmits to the application, upon receipt of a request (or automatically or based on a trigger event), data associated with one or more device design cases. In various embodiments, the data may include, but is not limited to: 1) device design files that are associated with a case; 2) information that associates a case with a particular surgeon, designer, device design and/or patient; 3) design modification information that tracks changes made to a device design; 4) fabrication timeline data that indicates, for example, when a device associated a case must be provided (e.g., as a finished, packaged product) to a surgeon.

In various embodiments, the application may include a designer portion and a surgeon portion. In some embodiments, the designer portion may allow a device designer to access design files and related data from one or more cases (e.g., commissions for a device). In one embodiment, the designer portion may anonymize (or may only include anonymized) patient data, thereby adhering to medical record confidentiality standards (e.g., such as HIPAA). In at least one embodiment, the surgeon portion may allow a surgeon to access design files and related data from one or more cases that are programmatically associated with the surgeon. Thus, in one or more embodiments, a surgeon and a designer may experience segregated portions while accessing the application.

Figure 7:
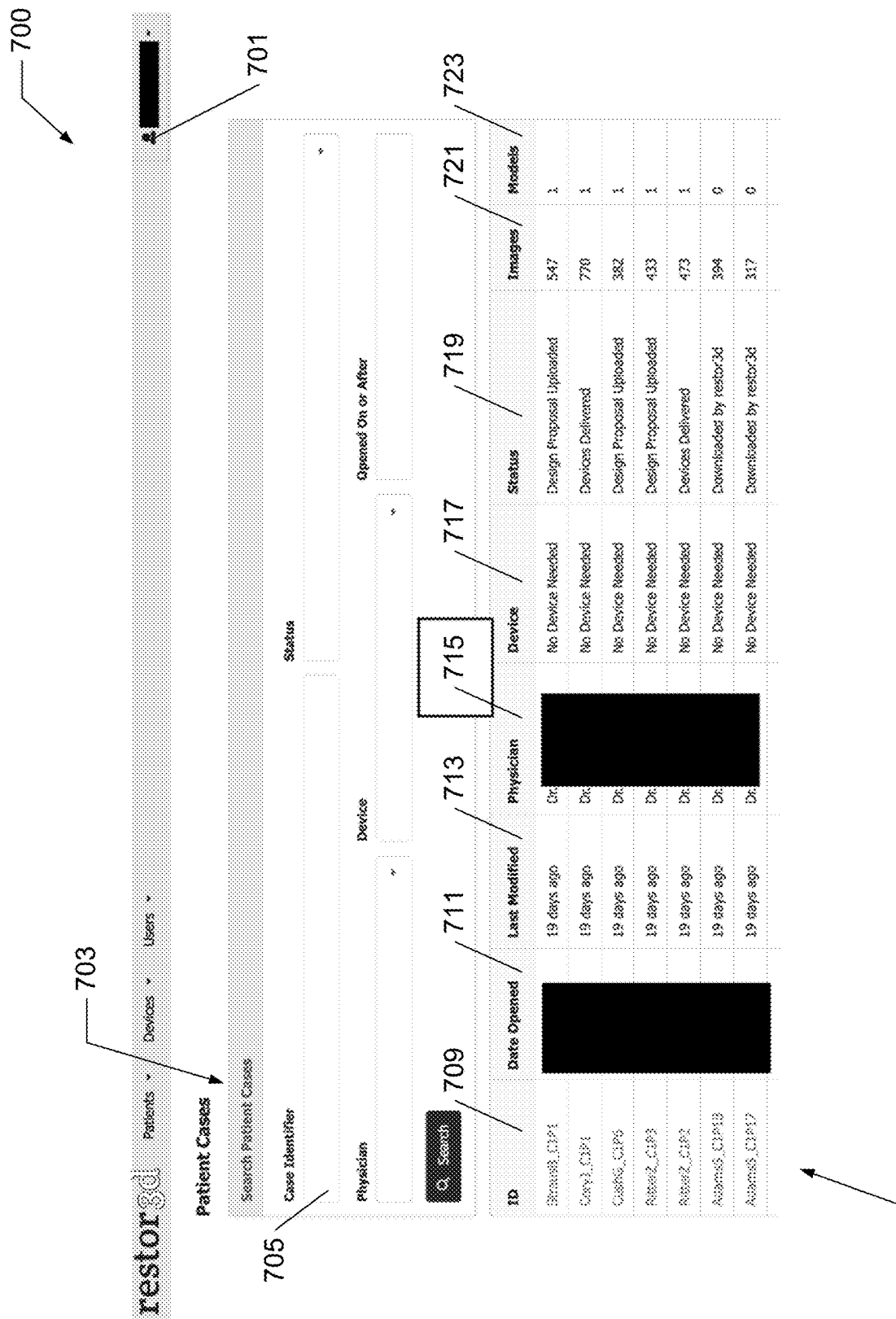
FIG. 7 is a screenshot of an exemplary custom device design service, according to one embodiment of the present disclosure.

As described herein, the application may include a design portion. FIG. 7 is a screenshot of an exemplary custom device design application that illustrates a designer portion 700. The design portion 700 may include a user feature 701 that indicates who is currently logged into the application. Accordingly, in one or more embodiments, the application may include a login page (not illustrated) that requires a designer, surgeon, and/or other user to provide login information to access an associated portion of the application (e.g., a design portion or a surgeon portion).

In at least one embodiment, the design portion 700 further includes a search feature 703 that allows a designer to search for cases that are associated with the designer. In some embodiments, the application may organize cases using a case identifier that uniquely associates a character string or other sequence with a designer, a surgeon, and a particular set of data (e.g., design files, etc.). Accordingly, the search feature 703 may include a case field 705 where a designer may enter a case identifier and, upon selecting a search button, be provided with data and files associated with the entered case identifier.

The design portion 700 may also include a results window 707 that provides an organized visualization of results returned from utilizing the search feature 703. The window 707 may organize case data by one or more categories including, but not limited to: 1) case ID 709; 2) an opening date 711 that may be a particular date a case was initiated by a surgeon and/or designer; 3) a last modified date 713 that may be a particular date that a case was last accessed (e.g., via the application); 4) a physician identifier 715 that may indicate a particular physician associated with a case; 5) a device identifier 717 that may indicate a particular device associated with a case; 6) a status indicator 719 that may provide a description of most recent activities and/or milestones associated with a case; 7) an images counter 721 that indicates how many images are associated with a case; and 8) a model counter 723 that indicates how many models (e.g., device design files) are associated with a case. In one or more embodiments, the design portion 700 may include a search feature 703 and a results window 707 that allow a designer to identify and inspect cases and case data that are programmatically associated with the designer.

As described herein, the application may include a surgeon portion. FIG. 8 is a screenshot of an exemplary custom device design application that illustrates a surgeon portion 800. The surgeon portion 800 further includes a search feature 801 that allows a designer to search for cases that are associated with the designer. In at least one embodiment, the application may organize cases using a patient name and a patient medical record number such that the patient name and record number are uniquely associated with surgeon, and/or a particular set of data (e.g., design files, etc.) stored by the application. Accordingly, the search feature 801 may include a patient name field 803 and/or a patient medical record number field 805 where a surgeon may enter a patient name and/or a patient medical record number, and, upon selecting a search button, be provided with data and files associated with the entered patient name and/or record number.

The design portion 800 may also include a results window 807 that provides an organized visualization of results returned from utilizing the search feature 801. The window 807 may organize case data by one or more categories including, but not limited to: 1) case ID 809; 2) an opening date 811 that may be a particular date a case was initiated by a surgeon and/or designer; 3) a last modified date 813 that may be a particular date that a case was last accessed (e.g., via the application); 4) a physician identifier 815 that may indicate a particular physician associated with a case; 5) a device identifier 817 that may indicate a particular device associated with a case; 6) a status indicator 819 that may provide a description of most recent activities and/or milestones associated with a case; 7) an images counter 821 that indicates how many images are associated with a case; and 8) a model counter 823 that indicates how many models (e.g., device design files) are associated with a case. Thus, in one or more embodiments, the surgeon portion 800 may include a search feature 801 and a results window 807 that allow a surgeon to identify and inspect cases and case data that are programmatically associated with the surgeon.

Figure 9:
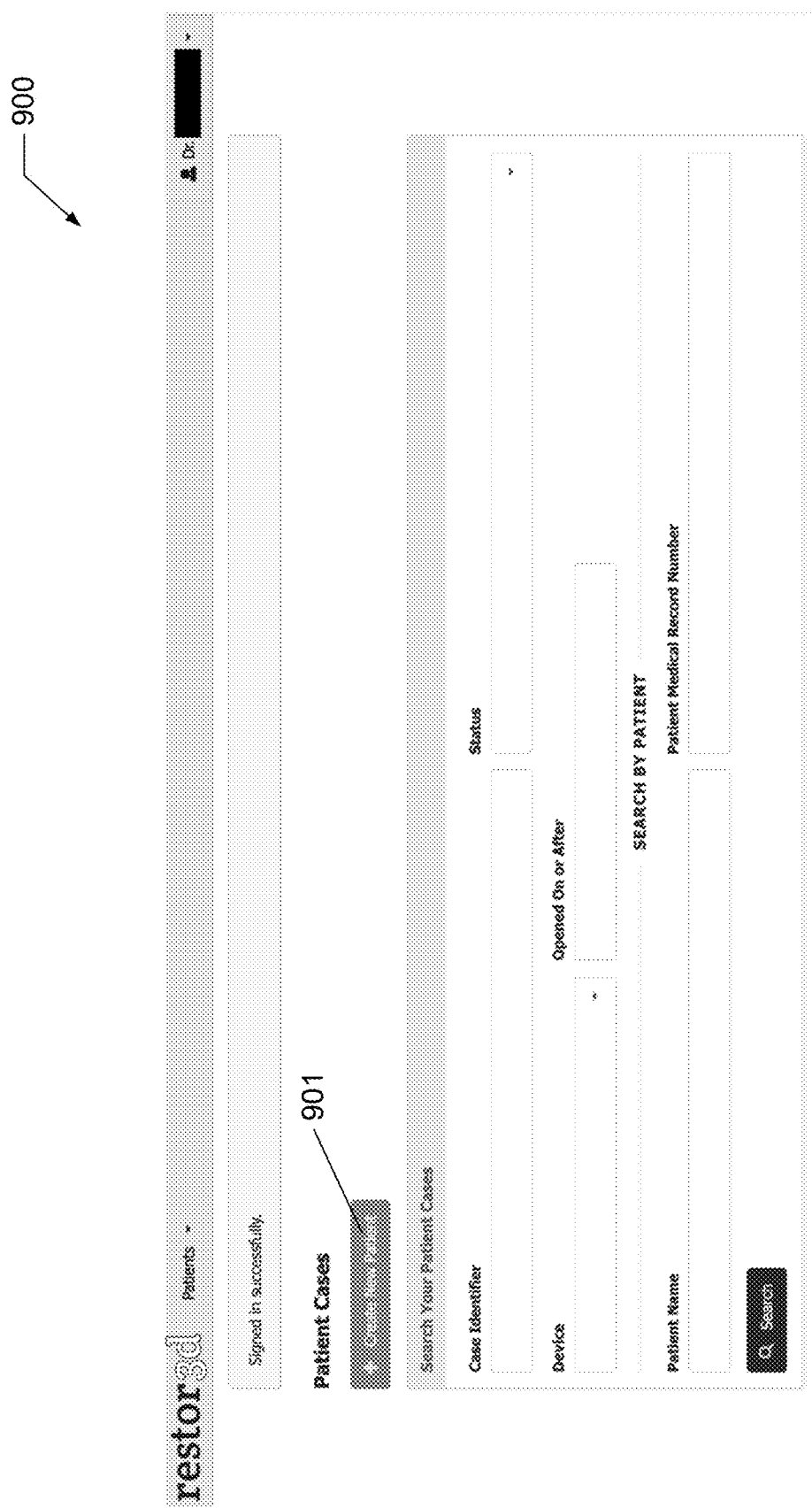
FIG. 9 is a screenshot of an exemplary custom device design service, according to one embodiment of the present disclosure.

FIG. 9 is a screenshot of an exemplary custom device design application that illustrates a surgeon portion 900. The surgeon portion 900 includes a patient creation button 901. In one or more embodiments, upon selection of the patient creation button 901, the application may initiate a new patient reception window (not illustrated). In at least one embodiment, the reception window may provide a surgeon with data entry fields for entering patient information. In various embodiments, the patient information may include, but is not limited to: 1) patient name; 2) patient medical record number; 3) a description of a patient condition and/or a patient diagnosis (each of which may be programmatically anonymized by the application); 4) patient images (e.g., sourced from medical imaging), such as one or more DICOM files; 5) a device design description; and 6) a device due date that indicates when a surgeon has elected to receive one or more fabricated custom devices. In at least one embodiment, a surgeon may select a "create" button within the reception window, and the application, upon detecting selection of the button, may automatically generate a new case and case identifier based on the entered patient information and information associated with the surgeon (e.g., that is stored within the application). In one or more embodiments, upon generating a new case, the application may automatically transmit a notification to at least one designer (e.g., associated with the application) that includes information regarding the new case (for example, a surgeon name and a case identifier). In at least one embodiment, the application may store contact information for any surgeon and any designer associated with the application, and the application may transmit electronic notifications (via a network) to any surgeon and/or designer using the stored information.

Figure 10:
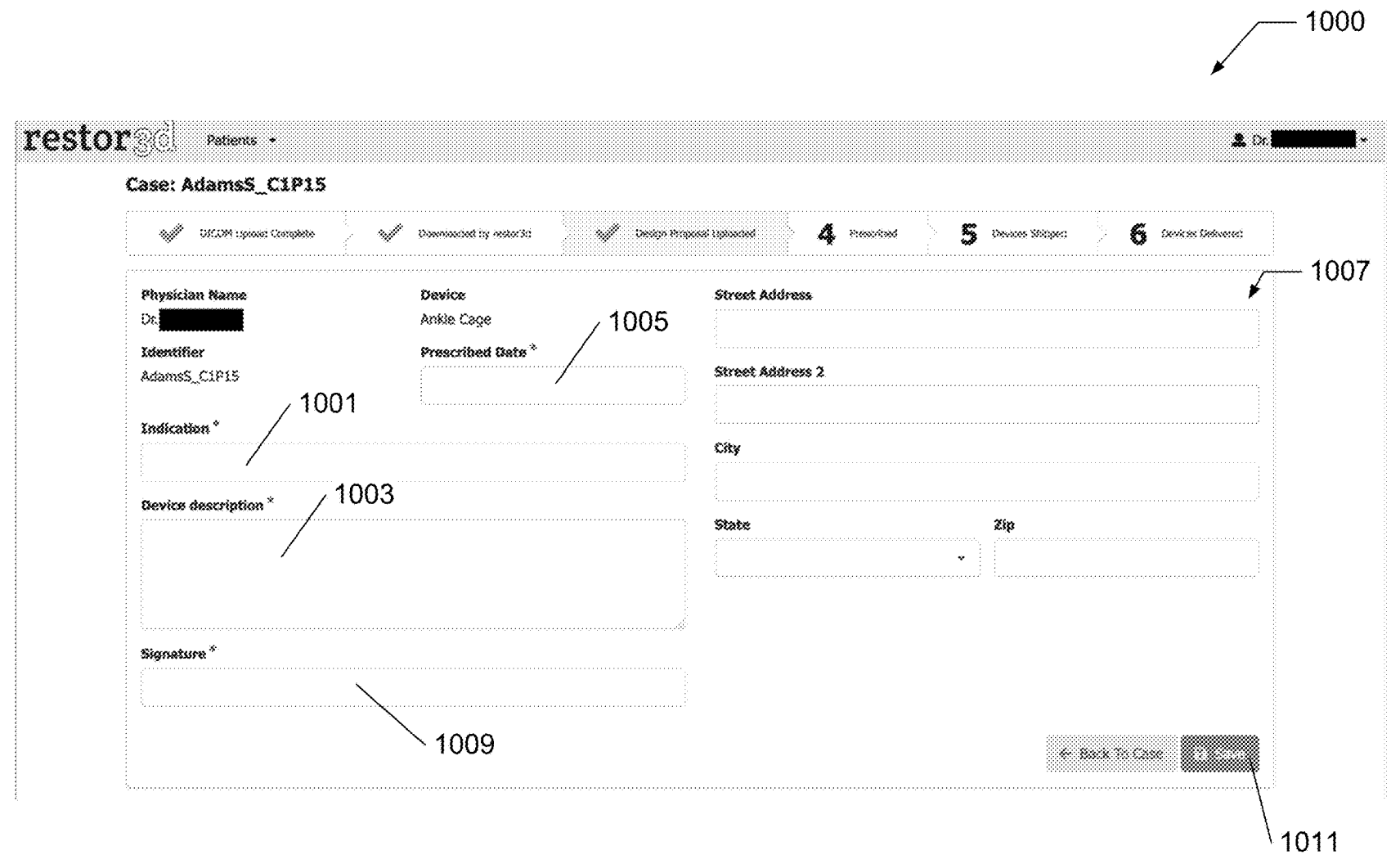

FIG. 10 is a screenshot of an exemplary custom device design application that illustrates a prescription form 1000 associated with a particular device design and fabrication case. In at least one embodiment, the prescription form 1000 may be provided in a surgeon portion (as described herein). In one or more embodiments, the prescription form 1000 may allow a surgeon to enter (in fields therein) information associated with a device design and fabrication request. The prescription form 1000 may provide data entry fields including, but not limited to: 1) an indication field 1001, into which a surgeon may enter an indication; 2) a device description field 1003, into which a surgeon may enter a description of a device to be designed and fabricated; 3) a prescribed date field 1005, into which a surgeon may enter a date indicating when a device is intended to be utilized in a surgical procedure; 4) one or more address fields 1007, into which a surgeon may enter a shipping destination for one or more fabricated custom devices; and 5) a signature field 1009, into which a surgeon may enter a signature that may be interpreted as an official commission for design and fabrication of one or more custom devices.

The prescription form 1000 may further include a save button 1011. In various embodiments, upon detection (by the application) that a surgeon has selected the save button 1011 (e.g., following data entry into one or more data fields), the application may automatically store all data entered in the prescription form 1000 and associated the stored data with a particular case.

Figure 11:
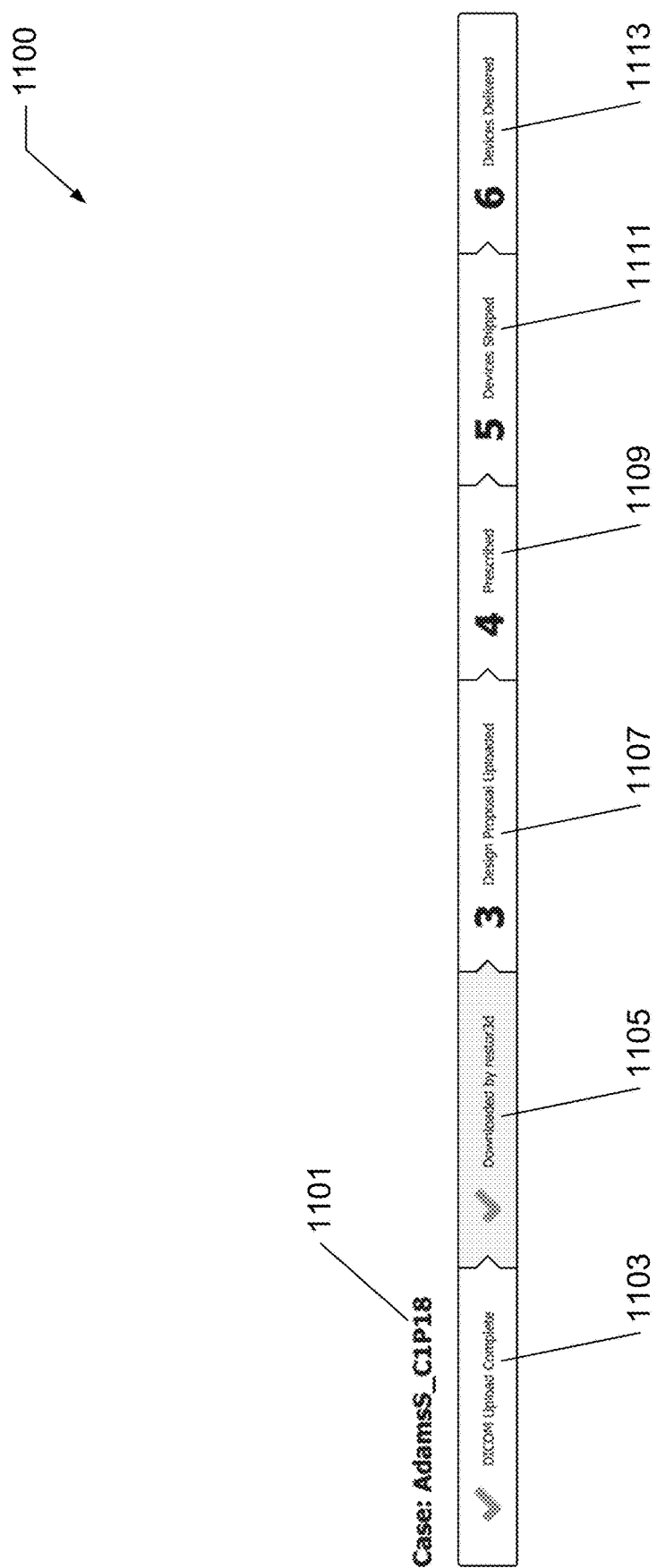
FIG. 11 is a screenshot of an exemplary custom device design service, according to one embodiment of the present disclosure.

FIG. 11 is a screenshot of an exemplary custom device design application that illustrates a case status indicator 1100. In various embodiments, the application may provide the case status indicator 1100 (e.g., on a website, in a notification, etc.) to a designer and/or a surgeon, where it may be interpreted as a visualization of progress (e.g., with respect to a custom device design and fabrication process). In one or more embodiments, the status indicator 1100 may document the progression of a case throughout a custom device design and fabrication process (as described herein). In at least one embodiment, the application may update the status indicator 1100 following receipt of a completion confirmation of one or more tasks. In various embodiments, the application may receive a completion confirmation in response to one or more tasks (associated with the device design and fabrication process) being completed. In one embodiment, a completion confirmation may be an electronic transmission (e.g., received at a server operatively connected to the application) that, when processed, causes the application to automatically update the status indicator 1100.

The status indicator 1100 may include one or more stages that are each associated with a particular task and/or phase of a custom device design and fabrication process. The one or more stages may include, but are not limited to: 1) a DICOM upload stage 1103; 2) a DICOM receipt stage 1105; 3) a design proposal upload stage 1107; 4) a prescription stage 1109; 5) a device shipment stage 1111; and 6) a device delivery stage 1113. In one or more embodiments, the DICOM upload stage 1103 may refer to an instance where a surgeon has successfully uploaded a patient medical image (e.g., a DICOM file) to the application. In at least one embodiment, the application may detect when a surgeon has successfully uploaded a patient medical image (e.g., that is associated with a case) and may update a status indicator (e.g., also associated with the case) to indicate that a DICOM upload stage has been completed.

In various embodiments, the DICOM receipt stage 1105 may refer to an instance where a designer (e.g., that is associated with a case) has successfully downloaded a patient medical image (also associated with the case) from the application. In at least one embodiment, the application may detect when a designer has successfully downloaded a patient medical image and may update an associated status indicator to indicate that a DICOM receipt stage has been completed.

In one or more embodiments, the design proposal upload stage 1107 may refer to an instance where a surgeon has successfully uploaded a design proposal to the application. In at least one embodiment, the application may detect when a surgeon has successfully uploaded a design proposal and may update a status indicator to indicate that a design proposal upload stage has been completed.

In various embodiments, the prescription stage 1109 may refer to an instance where a surgeon has successfully populated and submitted a prescription form (as described herein) to the application. In at least one embodiment, the application may detect when a surgeon has successfully submitted a prescription form (e.g., associated with a particular case) and may update an associated status indicator (also associated with the case) to indicate that a prescription stage has been completed.

In one or more embodiments, the device shipment stage 1111 may refer to an instance where a designer and/or a device fabricator (which may be the designer) has initiated shipment of one or more custom designed and fabricated devices. In at least one embodiment, the application may receive a transmission or a command (e.g., from a designer and/or fabricator) indicating that a device shipment process has been initiated and may update a status indicator to indicate that a device shipment stage has been completed.

In various embodiments, the device delivery stage 1113 may refer to an instance where a surgeon has received a shipment of one or more custom designed and fabricated devices. In at least one embodiment, the application may receive a transmission or a command (e.g., from a surgeon, shipment entity, etc.) indicating that a shipment of one or more custom devices has been delivered and may update a status indicator to indicate that a device delivery stage has been completed.

In one or more embodiments, the application may automatically generate an electronic stage completion notification following any update of a status indicator associated with a particular case. In at least one embodiment, the application may transmit, via a server and a network, the electronic stage completion notification to any surgeon and/or designer that is programmatically associated with the particular case. In various embodiments, the electronic stage completion notification may be an email, an electronic alert, a text message, or one or more additional electronic communication formats. In at least one embodiment, a status indicator may include one or more additional stages not illustrated in FIG. 11. For example, a status indicator may provide fields including, but not limited to: 1) a device utilization stage; 2) a device review stage; 3) a fabrication stage; 4) a device packaging stage; and 5) other stages related a custom device design and fabrication process.

In at least one embodiment, the application may include a design configuration form (which may be included in a prescription form described herein). In various embodiments, the design configuration form may include, but is not limited to: 1) a material selector that allows a surgeon to select a desired material from which a device may be fabricated; and 2) a radiopacity selector that allows a surgeon to select a desired radiopacity of a custom device to be designed and fabricated; and 3) a custom text and/or character window that allows a surgeon to enter one or more custom text and/or character selections to be included in a custom device design and integrally formed on one or more surfaces of a custom device. In at least one embodiment, the custom text and/or character window may include a 3D device design visualization and one or more data entry fields that allow a surgeon to enter a custom text and/or character selection and select a surface of a device design with which the selection will be integrally formed.

In one or more embodiments, the application may include a device visualization window that allows a surgeon and/or a designer to view, on a web browser and in three dimensions, one or more device design files. In at least one embodiment, the device visualization may be a live visualization of a device design editing suite currently in use by a designer. Thus, in one embodiment, the application may provide a surgeon with a live visualization of one or more device design files (e.g., as the one or more files are being edited by a designer). In various embodiments, the visualization window may allow a surgeon and/or a designer to lock the window and utilize one or more design annotation tools (provided by the application). In one embodiment, the annotation tools may include, but are not limited to: 1) a text-based commentary tool that allows a surgeon to insert comments directly into a design (or a rendering thereof); 2) a feature editing tool that allows a surgeon to manipulate one or more features of a design; and 3) a feature selection tool that allows a surgeon to highlight (e.g., via a color change) one or more features of a device design (or a rendering thereof).

In one or more embodiments, a device visualization window may further include and/or provide access to an exemplary virtual surgical environment. In one embodiment, the virtual surgical environment may include a rendering of an implant and/or other devices associated with a custom device. In at least one embodiment, the virtual surgical environment may provide a realistic visualization (such as an animation) of custom device implementation during an associated surgical procedure. In various embodiments, the virtual surgical environment may include a patient anatomy rendering that may be sourced from one or more patient medical images (e.g., DICOM files) that were uploaded to the application by the surgeon. In one or more embodiments, the virtual surgical environment may allow a surgeon and/or designer to visualize and evaluate performance of a custom medical device during an associated surgical procedure.

In various embodiments, the present systems and methods may include a production tracking module. In at least one embodiment, the production tracking module may be operatively connected to and/or communicate with a fabrication scheduling and management system, an inventory management system, and/or a workload management system. In one or more embodiments, the production tracking module may communicate with one or more systems that facilitate a custom device design and fabrication process.

In one embodiment, the production tracking module may integrate data received from the one or more systems and produce a holistic (or partial) visualization of the custom device fabrication process. In various embodiments, the production tracking module may be operative to configure and/or command one or more aspects of systems connected to the module. For example, the production tracking module may detect that a specific volume of a device design has been approved for fabrication (by a surgeon and/or designer) and may issue a command to an inventory management system that, upon receipt, causes the inventory system to assess and report if enough fabrication material is in stock to satisfy material demands of device fabrication. As another example, the production tracking module may detect that a device design has been approved for fabrication and may automatically issue a command to a fabrication scheduling and management system that, upon receipt, causes the system to initiate an additive manufacturing process and fabricate a specific volume of a device design. In one or more embodiments, the application may include a production tracking module that may coordinate any and/or all aspects of a custom device fabrication process.

In at least one embodiment, the production tracking module may receive fabrication data from a fabrication scheduling and management system. In various embodiments, the fabrication data may include, but is not limited to, fabrication production metrics and reports. In one or more embodiments, fabrication production metrics may include, but are not limited to: 1) amount of material utilized (e.g., to fabricate a device, a volume of devices, etc.); 2) scheduled fabrication time; 3) actual fabrication time; 4) scheduled fabrication down time; 5) unscheduled fabrication down time; 6) fabrication error rate; and 7) fabrication efficiency. In at least one embodiment, the production tracking module may generate one or more fabrication visualizations based on received fabrication data.

In various embodiments, the application may include one or more socialization and/or group features that allow one or more surgeons to be programmatically associated under a common group identifier. For example, the application may include a common group identifier for a specific surgical department of a hospital. In the same example, surgeons of the specific surgical department (e.g., that are users of the present application) may be provided access to anonymized versions of custom device designs commissioned by other surgeons within the specific surgical department. In at least one embodiment, the application may allow surgeons to form design groups and share anonymized versions of custom device designs, thereby potentially streamlining subsequent commissions for substantially similar and/or identical custom devices.

Description of Additional Methods for Fabricating Custom Devices

In one or more embodiments, doped resin, described herein, may present an increased viscosity (e.g., compared to viscosity of non-doped resin). In various embodiments, the present fabrication methods may include one or more techniques that compensate for the increased viscosity of the doped resin. In at least one embodiment, the one or more techniques may include, but are not limited to, introduction of additional doped resin to a reservoir of an additive manufacturing apparatus (such as a SLA 3D printer). For example, the present methods may include filling a resin reservoir in excess of an indicated filling volume. In an exemplary scenario, a cartridge (filled with resin) may be operatively connected to a resin reservoir. The resin may substantially drain from the cartridge into the resin reservoir, and the cartridge may be filled with additional resin to compensate for the drained resin. In one embodiment, because the doped resin viscosity is increased, the introduction of additional doped resin (e.g., above what an apparatus software/manufacturer deems necessary for a fabrication process) may compensate for the increased viscosity and resultant reduced flow (i.e., spread) of resin in the reservoir.

In various embodiments, to minimize post-processing workloads and material expenses, the present custom devices may be 3D printed without support structures. In one embodiment, the support structures can refer to 3D printed lattices, raftering and other structures that facilitate printing of a device, but are not themselves elements of the device. In one or more embodiments, to eliminate use of support structures, the present fabrication methods may include fabricating the present devices in a specific orientation such that the support structures are not required to achieve successful device fabrication. For example, the present devices may be fabricated (e.g., printed) in a vertical orientation that does not necessitate inclusion of support structures to achieve successful fabrication. Because the support structures are typically included to offset and compensate for temporarily intolerable stresses and strains experienced by a device during fabrication, a fabrication orientation may be selected such that all stresses and strains experience by a device during fabrication are tolerable. In at least one embodiment, a tolerable stress or strain can refer to stresses or strains that can be experienced by a device, during fabrication, without causing deformation of the device, or otherwise resulting in disruption and/or failure of the fabrication process.

In at least one embodiment, the present devices may be of sufficiently robust design such that printing (of a present device) can be performed in a vertical orientation and with a first layer of the present device in direct contact with a print bed. Typically, in previous methods, a device is printed at an angled orientation and, during printing, is not in direct contact with a print bed. For example, printing a device, by previous methods, may include orienting the device at a 30 degree angle (from vertical) and, prior to printing the device, printing a layer of support material directly onto a print bed (e.g., the support material buffering the device from the print bed). In the same example, the angled orientation and the support material may be required because the design of the previous device is insufficiently robust and, thus, if printed according to the present methods, would result in a faulty or failed device. In a contrasting example, printing a present device may include orienting the device at 0 degrees from vertical and printing the device directly atop a print bed, without printing a buffering support (or, in various embodiments, any supports). In the contrasting example, the design of the present device may be sufficiently robust to withstand any additional stresses and/or strains resulting from the vertical orientation and/or direct contact with the print bed. In various embodiments, vertical orientation, during printing of the present devices, may advantageously reduce and/or eliminate surface defects (e.g., as compared to previous devices and devices produced via previous methods). One of ordinary skill in the art will understand that surface defects (e.g., seams, cracks, voids, etc.) may undesirably present surfaces conducive to microbiological growth (e.g., bacterial growth, fungal growth, etc.) and/or foreign contaminants. Because the present devices may be absent such surface defects, the present devices may advantageously reduce a likelihood of microbiological growth and/or contamination on surfaces thereof.

Description of Additional Systems and Methods for Fabricating Autoclave-Able Custom Devices The following section describes one or more experimental tests, and results thereof, performed on one or more embodiments of the present system. The descriptions therein are provided for the purposes of illustrating various elements of the system (e.g., as observed in the one or more embodiments). All descriptions, embodiments, and the like are exemplary in nature and place no limitations on any embodiment described, or anticipated, herein.

Figure 12:
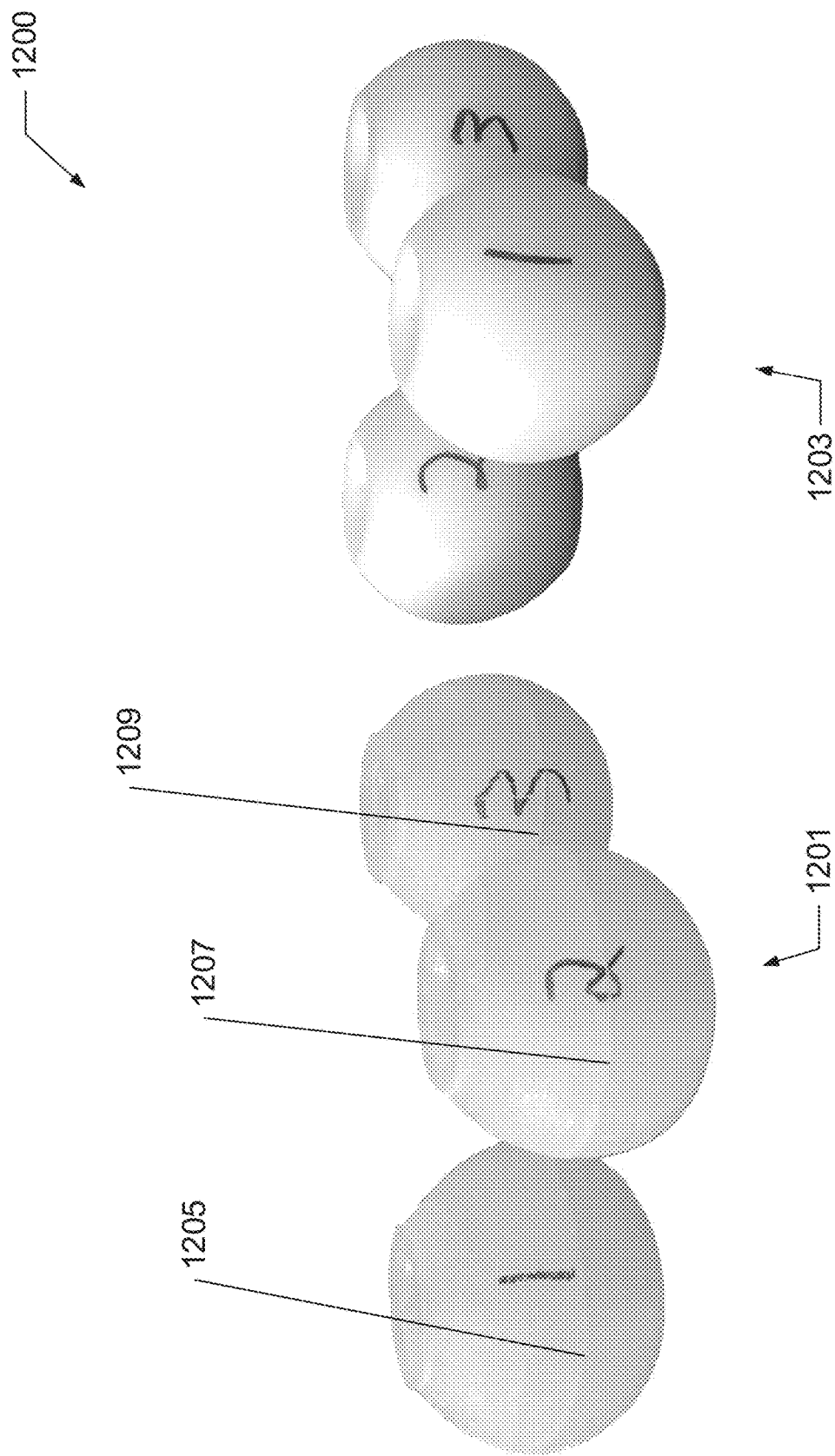
FIG. 12 is a photograph of exemplary autoclaved custom devices, according to one embodiment of the present disclosure.

As described herein, upon autoclaving the present devices, unexpected augmentation of one or more mechanical properties of the present devices was observed. The unexpected nature of these results may be further supported by FIG. 12. FIG. 12 illustrates experimental results 1200 including a control group 1201 and an experimental group 1203. The control group 1201 included three devices fabricated using a non-doped photo-curable resin. The experimental group 1203 included three devices fabricated using a barium sulfate-doped resin as described herein. Following fabrication, the control group 1201 and experimental group 1203 were each subjected to an autoclaving process.

In one embodiment, autoclaving processes may include steam autoclaving at a temperature of about 132 degree Celsius for about 4 minutes. In some embodiments, autoclaving processes may include 121 degrees Celsius for at least 30 minutes. In at least one embodiment, autoclaving processes may include a temperature of about 120-135 degrees Celsius for about 3-15 minutes.

Prior to acquiring the experimental results 1200, there was an expectation that doping of the resin with a contrast agent would not affect autoclave-ability of devices fabricated therefrom. At most, there was an expectation that doping of the resin with a contrast agent would render fabricated devices further unsuitable for autoclaving.

Following autoclaving, devices of the control group 1201 presented severe cracking, for example cracks 1205, 1207 and 1209, which would drastically compromise mechanical properties of the devices. In contrast, devices of the experimental group 1203 did not present cracking and, as described herein, demonstrate improved mechanical properties. Accordingly, the experimental results 1200 demonstrate that doping of a resin may render devices fabricated therefrom suitable for autoclaving. The experimental results 1200 were unexpected to one of ordinary skill in the art, because the addition of barium sulfate to the resin was expected to present no effect or, at most, a deleterious effect on autoclavability of devices produced therefrom. In at least one embodiment, suitability for autoclaving may refer to a capability of a device to withstand temperatures and pressures, of an autoclave apparatus, without presenting mechanical defects, such as cracks, or otherwise presenting compromised mechanical integrity. In one or more embodiments, following curing and autoclaving processes, the present devices may be substantially free of surface defects. For example, the present devices may be devoid of cracks and/or may present a high-quality surface finish (e.g., comparable to surface finishes demonstrated by injection molded components). In at least one embodiment, the present devices may include a non-breaking surface (e.g., devoid of defects, such as cracks, deformities, etc.). In various embodiments, the present devices (including doped resin) may present reduced surface roughness metrics, as compared to devices that do not include doped resin. For example, the present devices can demonstrate average roughness (Ra) and roughness range (Rz) metrics of lesser magnitude than Ra and Rz values demonstrated by devices that do not include doped resin.

Description of Additional Custom Device Features

In various embodiments, the present devices may include one or more features configured to improve fabrication outcomes. In at least one embodiment, because the present devices may be made from an initially liquid resin, instances may occur, during fabrication, wherein uncured resin undesirably remains within internal elements of a custom device. For example, the present devices may include a blind hole. In one embodiment, a blind hole refers to a hole that initiates at a surface of a device and that penetrates to a specified depth without breaking through the surface or another surface side of the device. In the same example, following fabrication, the blind hole may undesirably retain uncured resin. In one or more embodiments, to facilitate drainage of uncured resin, the present devices may include one or more drain ports that are integrally formed with the devices and that provide a route of egress for uncured resin to drain out of the devices. Continuing the same example, the undesirably retained uncured resin may flow out of one or more drain ports with which the device was integrally formed. In at least one embodiment, a drain port may be integrally formed with a blind hole (e.g., thereby transforming the blind hole into a through-hole).

In one or more embodiments, a drain port (as described herein) may include a first hole located at a distal or proximate end of a device, a second hole located between the distal and the proximate end of the device, and an internal, hollow shaft located within the device and operatively connecting the first hold and the second hole. In at least one embodiment, one or more portions of a drain port may include threads. For example, a first hole may include one or more threads (e.g., for receiving a threaded element, such as a threaded rod). In various embodiments, the first hold, second hole, and shaft may include a generally cylindrical cross-section. In at least one embodiment, a slope and/or curvature of the shaft may be optimized to facilitate drainage of uncured resin (from the device) out the second and/or first hole. For example, the shaft may include a curvature (e.g., a bend) that directs uncured resin towards the second hole. In the same example, the shaft may further include a slope that, in combination with the curvature, establishes a path of least resistance directing flow of fluid (e.g., uncured resin) out of the device, via the second hole. In at least one embodiment, a curvature of the shaft may measure between about 5-75 degrees (e.g., with respect to a medial axis thereof).

Figure 13:
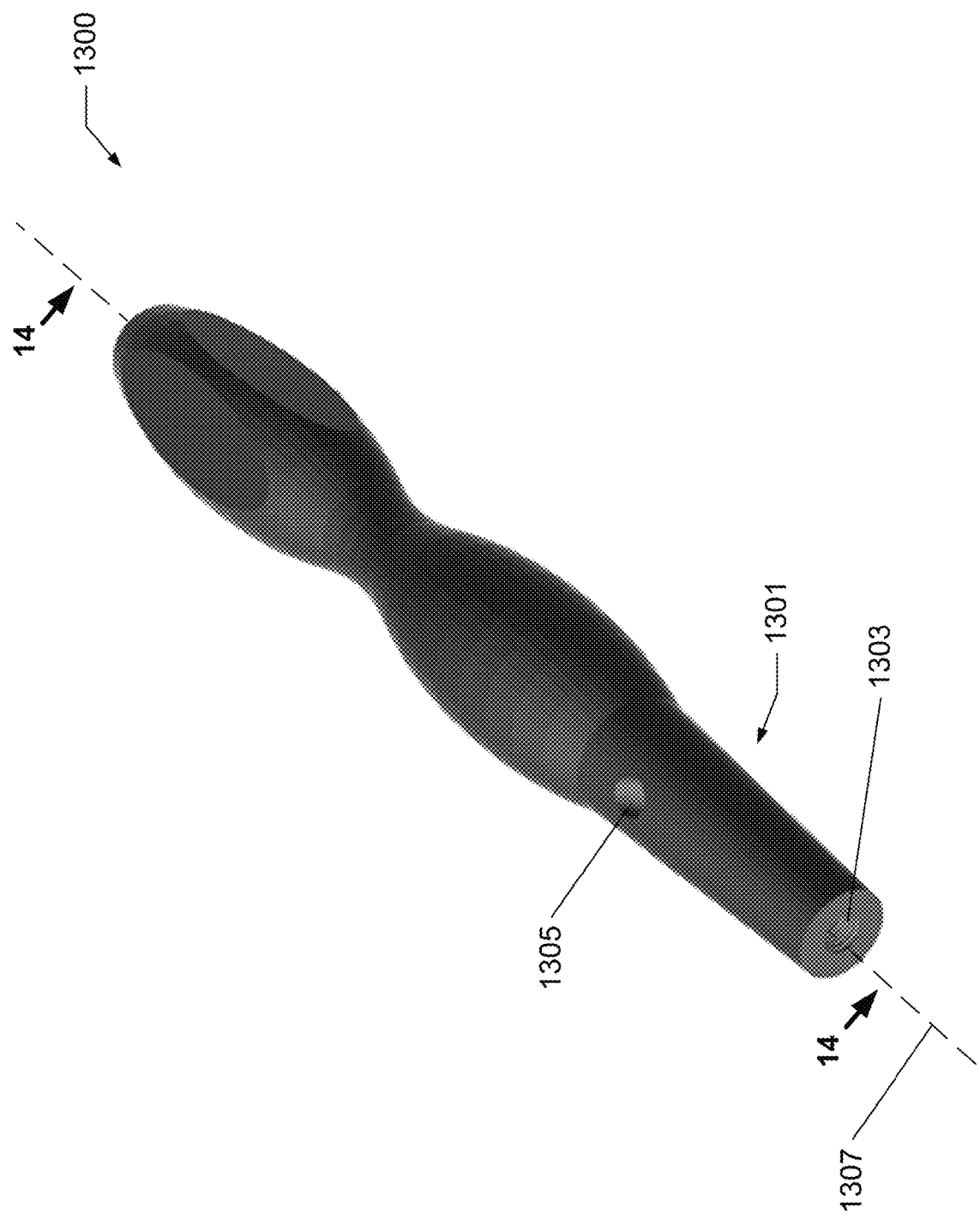
FIG. 13 shows a perspective view of an exemplary custom device, according to one embodiment of the present disclosure.
Figure 14:
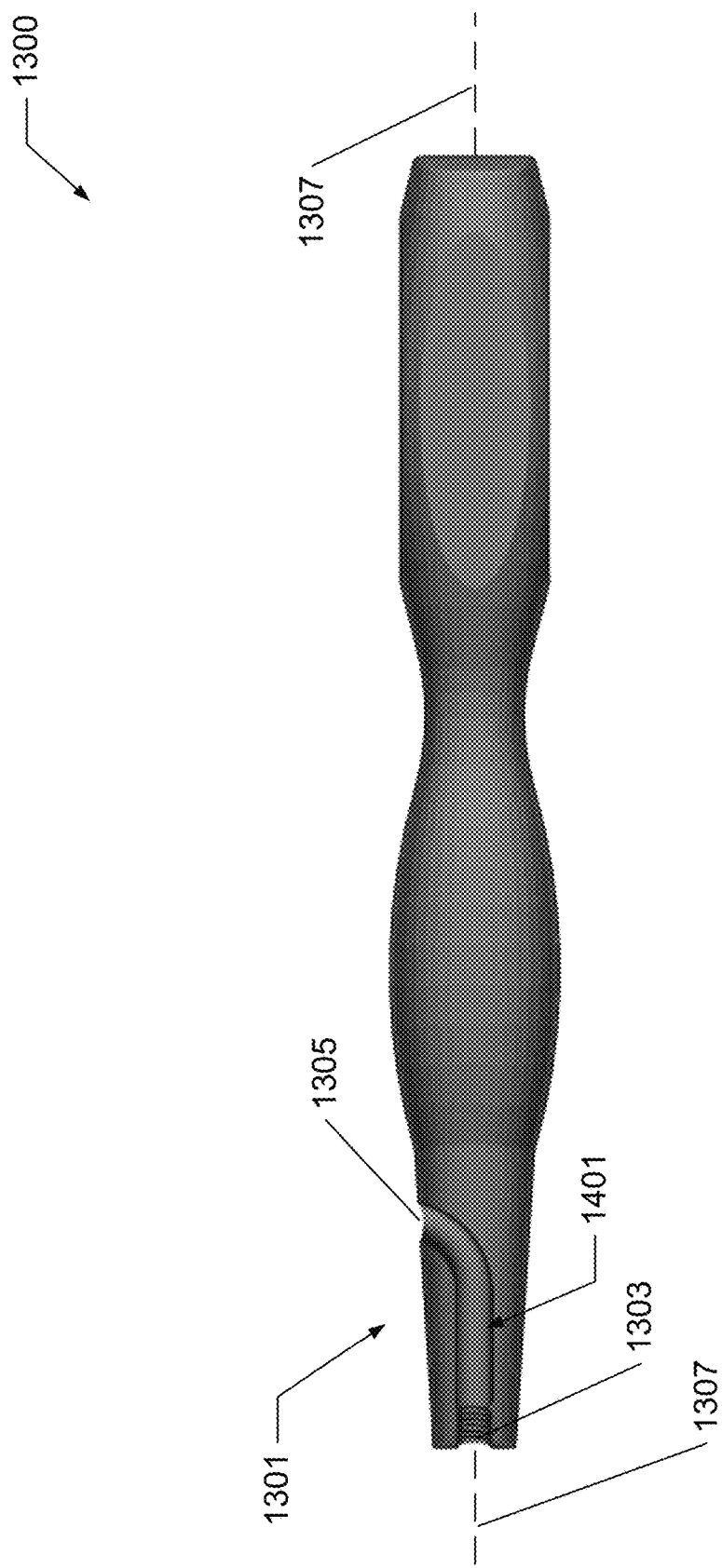
FIG. 14 shows a cross-sectional view of an exemplary device, according to one embodiment of the present disclosure.

FIG. 13 shows a perspective view of an exemplary device 1300. In at least one embodiment, the device 1300 includes a drain port 1301. The drain port 1301 may include a first hole 1303, a second hole 1305, and a hollow shaft 1401 (FIG. 14). In one or more embodiments, the drain port 1301 may be centered along a medial axis 1307. In various embodiments, uncured resin within the drain port 1301 may drain outward, from the device 1300, via shaft 1307 and the second hole 1305 and/or first hole 1303.

FIG. 14 shows a sectional view of an exemplary device 1300. The device 1300 can include a drain port 1301 including a first hole 1303, a second hole 1305, and a hollow shaft 1401. In various embodiments, the hollow shaft 1401 may connect the first hole 1303 and the second hole 1305 in a manner such that resin may flow therebetween and therefrom (e.g., out of the device 1300).

CONCLUSION

Aspects, features, and benefits of the systems, methods, processes, formulations, apparatuses, and products discussed herein will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a computer to perform one specific function or a group of functions.

Those skilled in the art will understand the features and aspects of a suitable computing environment in which aspects of the disclosure may be implemented. Although not required, some of the embodiments of the claimed inventions may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

We claim:

1. A method for producing disposable, radiopaque devices comprising:
    normalizing a quantity of barium sulfate particles, wherein normalizing comprises milling and sieving the quantity of barium sulfate particles;
    mixing a substantially homogenous photo-curable mixture comprising approximately 1-10% weight percent of the normalized barium sulfate particles and approximately 90-99% weight percent of a photo-curable resin, wherein:
        the photo-curable mixture has a higher viscosity than the photo-curable resin;
        the photo-curable resin comprises a pre-cure ultimate tensile strength between about 12.0-32.0 MPa; and
        the photo-curable resin comprises a pre-cure heat deflection temperature less than or equal to about 35 degrees Celsius;
    3D printing the photo-curable mixture in a particular shape by:
        mixing the photo-curable mixture via a wiper arm; and
        printing the photo-curable mixture in the particular shape;
    curing the 3D-printed photo-curable mixture in the particular shape by heating the 3D-printed photo-curable mixture and bathing the 3D-printed photo-curable mixture in light to create a radiopaque device comprising a first ultimate bending strength and a first bending yield strength; and
    autoclaving the radiopaque device, wherein:
        the autoclaved, radiopaque device comprises:
            a second ultimate bending strength and a second bending yield strength;
            an ultimate tensile strength between about 26-32 MPa; and
            a tensile yield strength between about 16-25 MPa;
        the second ultimate bending strength is greater than the first ultimate bending strength; and
        the second bending yield strength is greater than the first bending yield strength.

2. The method for producing disposable, radiopaque devices of claim 1, wherein:
    the second ultimate bending strength is about 4-10% greater than the first ultimate bending strength; and
    the second bending yield strength is about 5-9% greater than the first bending yield strength.

3. The method for producing disposable, radiopaque devices of claim 1, wherein curing the 3D-printed photo-curable mixture comprises:
    heating the radiopaque 3D-printed photo-curable mixture to about 60 degrees Celsius; and
    bathing the radiopaque 3D-printed photo-curable mixture in about 405 nm light.

4. The method for producing disposable, radiopaque devices of claim 3, wherein autoclaving the radiopaque device comprises steam autoclaving the radiopaque device at a temperature of about 132 degrees Celsius.

5. The method for producing disposable, radiopaque devices of claim 4, wherein the substantially homogenous photo-curable mixture is mixed in a mixer with sharp blades.

6. The method for producing disposable, radiopaque devices of claim 5, wherein the photo-curable mixture is printed via a stereolithography 3D-printer.

7. The method for producing disposable, radiopaque devices of claim 6, wherein the autoclaved, radiopaque device is viewable via at least one radiative imaging technique.

8. The method for producing disposable, radiopaque devices of claim 7, wherein the radiopaque device comprises a drain port.

9. The method for producing disposable, radiopaque devices of claim 8, wherein the drain port is integrally formed within the radiopaque device.

10. The method for producing disposable, radiopaque devices of claim 9, wherein the drain port comprises:
    a generally cylindrical cross-section; and
    at least one bend.

11. The method for producing disposable, radiopaque devices of claim 10, wherein the drain port comprises one or more threads.

12. The method for producing disposable, radiopaque devices of claim 8, further comprising draining uncured photo-curable mixture from the radiopaque device via the drain port.

13. A method for producing disposable, radiopaque devices comprising:
    mixing a substantially homogenous photo-curable mixture comprising approximately 1-10% weight percent of the radiographic contrast agent particles and approximately 90-99% weight percent of a photo-curable resin, wherein:
        the photo-curable mixture has a higher viscosity than the photo-curable resin;
        the photo-curable resin comprises a pre-cure ultimate tensile strength between about 12.0-32.0 MPa; and
        the photo-curable resin comprises a pre-cure heat deflection temperature less than or equal to about 35 degrees Celsius;
    3D printing the photo-curable mixture in a particular shape;
    curing the 3D-printed photo-curable mixture in the particular shape by heating the 3D-printed photo-curable mixture and bathing the 3D-printed photo-curable mixture in light to create a radiopaque device comprising a first ultimate bending strength and a first bending yield strength; and
    autoclaving the radiopaque device, wherein:
        the autoclaved, radiopaque device comprises:
            a second ultimate bending strength and a second bending yield strength;
            an ultimate tensile strength between about 26-32 MPa; and
            a tensile yield strength between about 16-25 MPa;
        the second ultimate bending strength is greater than the first ultimate bending strength; and
        the second bending yield strength is greater than the first bending yield strength.

14. The method for producing disposable, radiopaque devices of claim 13, wherein curing the 3D-printed photo-curable mixture comprises:
    heating the radiopaque 3D-printed photo-curable mixture to about 60 degrees Celsius; and
    bathing the radiopaque 3D-printed photo-curable mixture in about 405 nm light.

15. The method for producing disposable, radiopaque devices of claim 14, wherein autoclaving the radiopaque device comprises steam autoclaving the radiopaque device at a temperature of about 132 degrees Celsius.

16. The method for producing disposable, radiopaque devices of claim 15, wherein the substantially homogenous photo-curable mixture is mixed in a mixer with sharp blades.

17. The method for producing disposable, radiopaque devices of claim 16, wherein the photo-curable mixture is printed via a stereolithography 3D-printer.

18. The method for producing disposable, radiopaque devices of claim 17, wherein the autoclaved, radiopaque device is viewable via at least one radiative imaging technique.

19. The method for producing disposable, radiopaque devices of claim 18, wherein the radiopaque device comprises a drain port.

20. The method for producing disposable, radiopaque devices of claim 19, wherein the drain port is integrally formed within the radiopaque device.

21. The method for producing disposable, radiopaque devices of claim 20, wherein the drain port comprises:
a generally cylindrical cross-section; and
at least one bend.

22. The method for producing disposable, radiopaque devices of claim 21, wherein the drain port comprises one or more threads.

23. The method for producing disposable, radiopaque devices of claim 21, further comprising draining uncured photo-curable mixture from the radiopaque device via the drain port.

24. The method for producing disposable, radiopaque devices of claim 13, further comprising normalizing a quantity of radiographic contrast agent particles, wherein normalizing comprises milling and sieving the quantity of radiographic contrast agent particles.

25. The method for producing disposable, radiopaque devices of claim 13, wherein the radiographic contrast agent particles comprise barium sulfate particles.

* * * * *